(12) United States Patent
Chiang et al.

(10) Patent No.: US 8,270,559 B2
(45) Date of Patent: Sep. 18, 2012

(54) METHOD AND SYSTEM FOR TOMOGRAPHIC RECONSTRUCTION IN MEDICAL IMAGING USING THE CIRCLE AND LINE TRAJECTORY

(75) Inventors: Be-Shan S. Chiang, Buffalo Grove, IL (US); Alexander A. Zamyatin, Buffalo Grove, IL (US); Satoru Nakanishi, Utsunomiya (JP); Michael D. Silver, Northbrook, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 808 days.

(21) Appl. No.: 12/445,757

(22) PCT Filed: Nov. 26, 2007

(86) PCT No.: PCT/US2007/085510
§ 371 (c)(1),
(2), (4) Date: Apr. 16, 2009

(87) PCT Pub. No.: WO2008/064367
PCT Pub. Date: May 29, 2008

(65) Prior Publication Data
US 2010/0283779 A1 Nov. 11, 2010

Related U.S. Application Data

(60) Provisional application No. 60/867,165, filed on Nov. 24, 2006.

(51) Int. Cl.
*A61B 6/00* (2006.01)

(52) U.S. Cl. .......................................................... 378/4
(58) Field of Classification Search ........................ 378/4
See application file for complete search history.

(56) References Cited

U.S. PATENT DOCUMENTS 5,170,439 A * 12/1992 Zeng et al. ................... 382/131
(Continued)

FOREIGN PATENT DOCUMENTS

JP 2001-327514 11/2001
(Continued)

OTHER PUBLICATIONS

Hu, Exact Regional Reconstruction of Longitudinally-Unbounded Objects Using the Circle=and-Line Cone Beam Tomographic System, SPIE vol. 3032, 1997, pp. 441-444.*

(Continued)

*Primary Examiner* — Alexander H Taningco
(74) *Attorney, Agent, or Firm* — Oblon, Spivak, McClelland, Maier & Neustadt, L.L.P.

(57) ABSTRACT

A method of reconstructing a volume image of an object includes receiving circle projection data collected by a detector along a circular path with respect to the object; receiving line projection data collected by the detector along a linear path with respect to the object; producing a reconstructed circle path volume image of the object from the pre-processed circle projection data using a reconstruction algorithm that includes a ramp filter; producing a reconstructed line path volume image of the object from pre-processed line projection data using a reconstruction algorithm that includes a Hubert filter; and combining the reconstructed circle path volume image and the reconstructed line path volume image to produce the volume image of the object. An apparatus and computer program product are also described.

33 Claims, 34 Drawing Sheets

U.S. PATENT DOCUMENTS

| | | | |
|---|---|---|---|
| 5,784,481 A * | 7/1998 | Hu | 382/131 |
| 6,014,419 A * | 1/2000 | Hu | 378/4 |
| 6,148,056 A * | 11/2000 | Lin et al. | 378/4 |
| 6,330,298 B1 | 12/2001 | Tam | |
| 6,560,308 B1 * | 5/2003 | Zmora | 378/4 |
| 2003/0161443 A1 | 8/2003 | Xiao et al. | |
| 2004/0252806 A1 | 12/2004 | Taguchi et al. | |
| 2006/0034417 A1 * | 2/2006 | Katsevich | 378/4 |
| 2006/0050842 A1 | 3/2006 | Wang et al. | |
| 2006/0067457 A1 | 3/2006 | Zamyatin et al. | |
| 2006/0104407 A1 | 5/2006 | Zamyatin et al. | |

FOREIGN PATENT DOCUMENTS

| | | |
|---|---|---|
| JP | 2002-282246 | 10/2002 |
| JP | 2003-144428 | 5/2003 |
| JP | 2003-199740 | 7/2003 |
| JP | 2005-296469 | 10/2005 |
| JP | 2006-87921 | 4/2006 |
| JP | 2006-95297 | 4/2006 |
| JP | 2006-288472 | 10/2006 |
| JP | 2008-512145 | 4/2008 |
| WO | 2007/119124 | 10/2007 |

OTHER PUBLICATIONS

Zamyatin et al., Implementation of the circle-and-line algorithm for 256-detector row CT, Medical Imaging 2007: Physics of Medical Imaging, Proc of SPIE vol. 6510, 2007, pp. 1-9.*

Office Action issued Jul. 31, 2012 in Japanese Patent Application No. 2009-538528, with English translation.

* cited by examiner

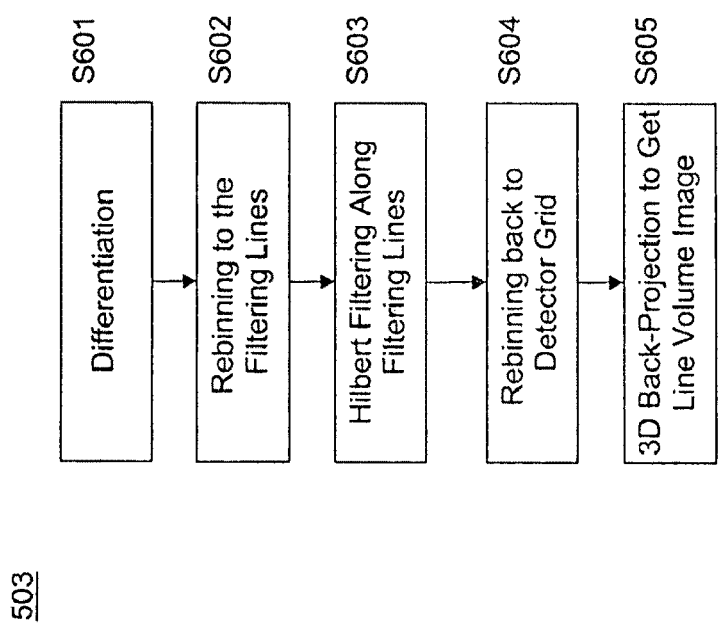

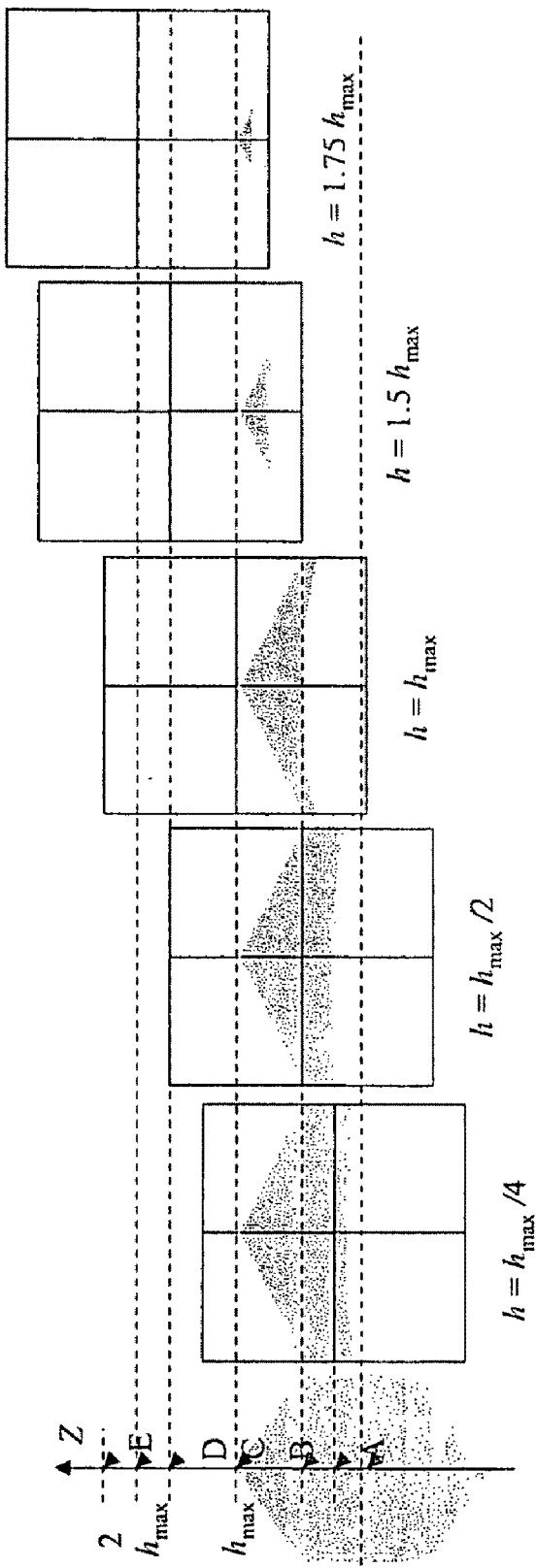

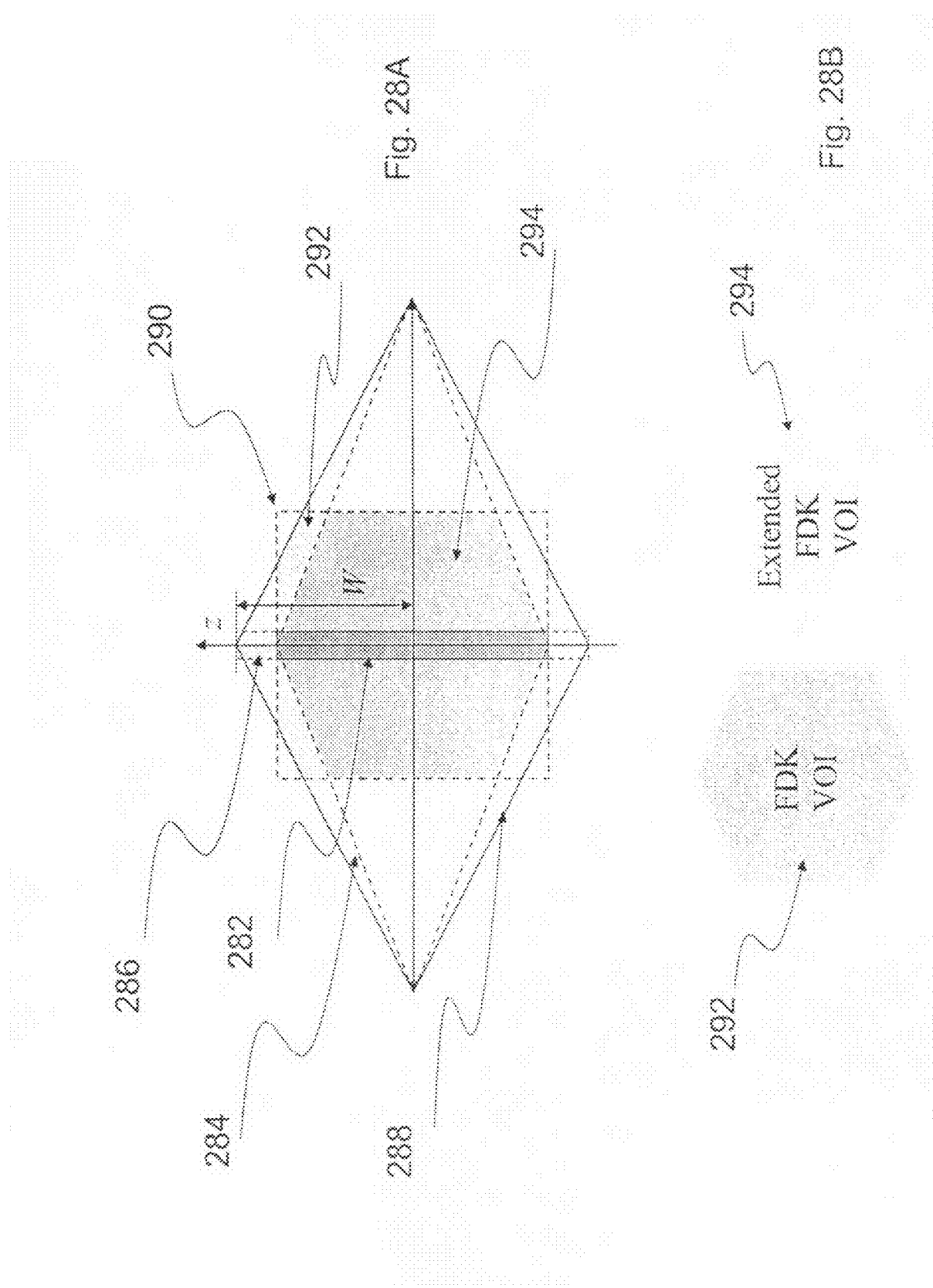

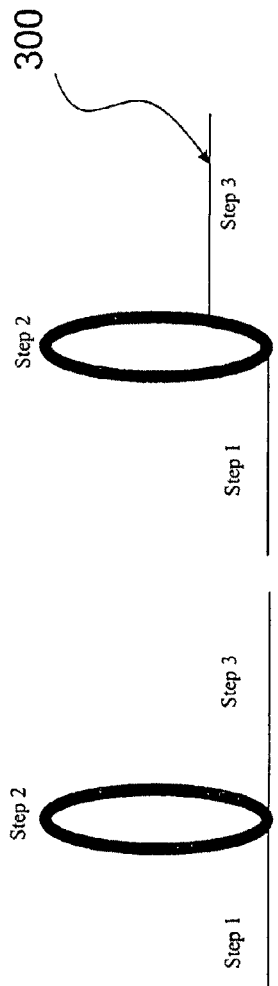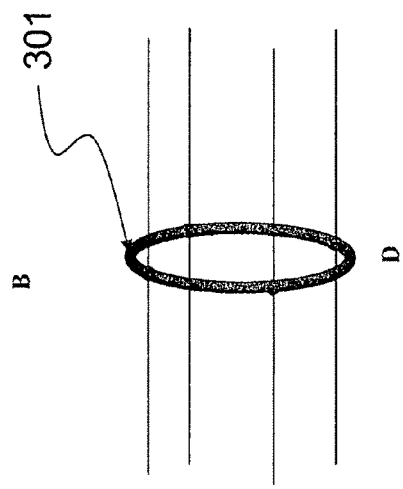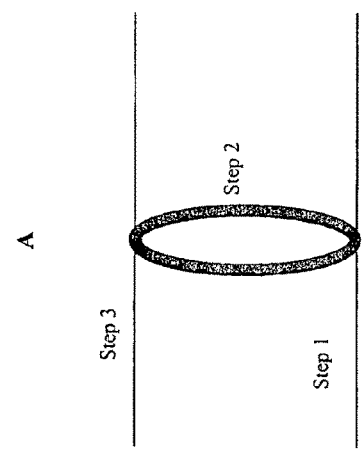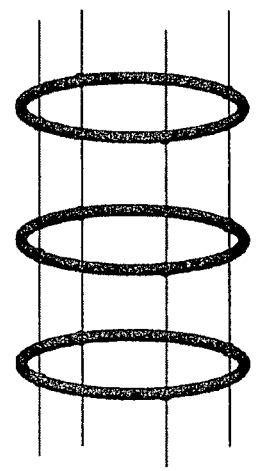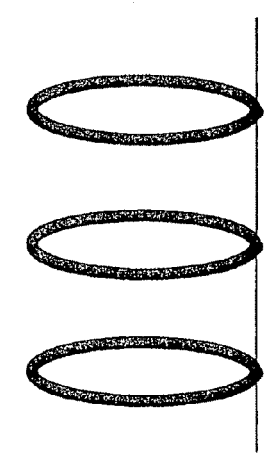
Fig. 29A Fig. 29B Fig. 29C Fig. 29D Fig. 29E Fig. 29F

METHOD AND SYSTEM FOR TOMOGRAPHIC RECONSTRUCTION IN MEDICAL IMAGING USING THE CIRCLE AND LINE TRAJECTORY

BACKGROUND OF THE INVENTION

Field of the Invention

The present invention relates generally to the reconstruction of medical images. More specifically, the present invention relates to a new method and system apparatus for improving medical image quality and efficiency using 3D cone beam computed tomography (CT) reconstruction based on projection data from circle and line trajectory scans.

LIST OF REFERENCES

The present invention includes the use of various technologies referenced and described in the documents identified in the following LIST OF REFERENCES, which are cited throughout the specification by the corresponding reference number in brackets and are incorporated by reference herein in their entirety:

[1] M. Endo, S. Mori, T. Tsunoo, S. Kandatsu, S. Tanada, H. Aradate, Y. Saito, H. Miyazaki, K. Satoh, S. Matsusita, M. Kusakabe, Development and performance evaluation of the first model of 4DCT scanner, *IEEE Trans. Nuclear Science*, vol. 50, pp.1667-1671, 2003.

[2] S. Mori, M. Endo, T. Tsunoo, S. Kandatsu, S. Tanada, H. Aradate, Y. Saito, H. Miyazaki, K. Satoh, S. Matsushita, M. Kusakabe, Physical performance evaluation of a 256-slice CT-scanner for four-dimensional imaging, *Medical Physics*, Vol. 31 (6), pp. 1348-1356, June 2004.

[3] S. Mori, M. Endo, R. Kohno, S. Minohara, K. Kohno, H. Asakura, H. Fujiwara, K. Murase, Respiratory-gated segment reconstruction for radiation treatment planning using 256-slice CT-scanner during free breathing, *Medical Imaging 2005: Visualization, Image-Guided Procedures, and Display*, (Edited by Robert L. Jr. Galloway and Kevin R. Cleary), *Proceedings of the SPIE*, Vol. 5745, pp. 711-721, 2005.

[4] S. Mori, M. Endo, K. Nishizawa, K. Murase, H. Fujiwara, and S. Tanada, Comparison of patient doses in 256-slice CT and 16-slice CT scanners, *The British Journal of Radiology*, vol. 79, pp. 56-61, 2006.

[5] L. A. Feldkamp, L. C. Davis, and J. W. Kress. Practical cone-beam algorithm, *J. Opt. Soc. Am*, vol. 1, pp. 612-619, 1984.

[6] G. L. Zeng and G. T. Gullberg, A cone-beam tomography algorithm for orthogonal circle-and-line orbit *Phys. Med. Biol.*, vol. 37, 563-77, 1992.

[7] H. Kudo and T. Saito, Derivation and implementation of a cone-beam reconstruction algorithm for nonplanar orbits, *IEEE Trans. Med. Imaging*, vol. 13, pp. 196-211, 1994.

[8] H. Hu, A new cone beam reconstruction algorithm for the circle-and-line orbit *Proc. 1995 Int. Meeting on Fully 3D Image Reconstruction in Radiology and Nuclear Medicine* (Aixles-Bains, France, Jul. 4-6, 1995) ed P Grangeat (Grenoble: LETI) pp 303-10, 1995.

[9] R. H. Johnson, H. Hu, S. T. Haworth, P. S. Cho, C. A. Dawson, and J. H. Linehan, Feldkamp and circle-and-line cone-beam reconstruction for 3D micro-CT of vascular networks, *Phys. Med. Biol.*, vol. 43, pp. 929-940, 1998.

[10] F. Noo, M. Defrise, and R. Clack, Direct reconstruction of cone-beam data acquired with a vertex path containing a circle, *IEEE Trans. Medical Imaging*, vol. 7, no. 6, pp. 854-867, 1998.

[11] A. Katsevich, Image reconstruction for the circle and line trajectory, *Phys. Med. Biol.*, vol. 49, pp. 5059-5072, 2004.

[12] A. A. Zamyatin, K. Taguchi, and M. D. Silver, Practical hybrid convolution algorithm for helical CT reconstruction, *IEEE Trans. Nuclear Sciences*, 53 (1), pp. 167-174, 2006.

[13] A. Katsevich, K. Taguchi, and A. A. Zamyatin, Formulation of four Katsevich algorithms in native geometry, *IEEE Trans. Medical Imaging*, vol. 25, no. 7, pp. 855-868, July 2006.

[14] P. Koken, C. Bontus, T. Kohler, and M. Grass, Cardiac cone-beam CT using a circle and line acquisition and an exact reconstruction, *IEEE Nuclear Science Symposium Conference Record*, M08-5, 2005.

[15] A. A. Zamyatin and K. Taguchi, U.S. Patent Publication # 20060067457, Ser. No. 10/951,650, filed Sep. 29, 2004.

[16] A. A. Zamyatin, K. Taguchi and M. D. Silver, "Practical Hybrid Convolution Algorithm for Helical CT Reconstruction", *IEEE Transactions on Nuclear Sciences*, vol. 53, no. 1, pages 167-174, February 2006. doi:10.1109/TNS.2005.862973

[17] D. L. Parker, Optimal short scan convolution reconstruction for fan beam CT, *Med. Phys.* 9 (2)0982, 254-257.

[18] M. D. Silver, A method for including redundant data in computed tomography, *Med. Phys.*, 27, 773-774, 2000.

[19] F. Noo, M. Defrise, R. Clackdoyle, H. Kudo, Image reconstruction from fan-beam projections on less then a short scan, *Phys. Med. Biol.*, 47, 2525-2546, 2002.

DISCUSSION OF BACKGROUND

The quality and efficiency of a reconstructed image created by a computed tomography (CT) device are important to the overall effectiveness of the CT device. The algorithm used in reconstructing the image impacts quality and efficiency.

In addition, there is a clinical demand for a CT scanner that covers a whole human organ in one rotation in circular acquisitions. Circular trajectory has advantages over helical for dynamic studies, such as cardiac/coronary artery imaging, perfusion, etc. Note that, for example, to cover a human heart requires a detector size of 10-12 centimeters in the axial direction.

To scan most human organs in just one rotation, a scanner with a large volume coverage is required. Such large volume coverage is a challenge for the conventional approximate or non-exact reconstruction method based on the algorithm of Feldkamp, Davis, Kress (FDK) [5] that is widely used in medical CT.

FDK is an efficient way to reconstruct the circular x-ray CT data with high achievable spatial resolution, while other algorithms involve some steps, such as rebinning, which may degrade the special resolution. However, the cone beam geometry of FDK suffers from cone beam artifacts due to theoretical incompleteness of the circle trajectory, especially in places of rapid attenuation change in the longitudinal direction.

On the other hand, an exact filtered-backprojection (FBP) reconstruction algorithm has also been proposed [11]. It is known that exact reconstruction of the cone beam data is impossible when the x-ray trajectory consists of a single circle, because there are many planes that do not intersect the trajectory and data within these planes is not measured. In other words, circle data 12 provides incomplete Radon space coverage in region 10, for example as shown in FIG. 1. To overcome this restriction, it has been suggested to augment a circle scan trajectory 22 with a line scan trajectory 20, as shown in FIG. 2, and various circle-and-line algorithms have been proposed [6-10]. However, algorithms proposed in [6]-[10] were not very suitable for implementation in commercial CT scanners, mainly because of two factors: (a) they require a long time for image reconstruction due to inefficient structure of those algorithms (they were not of the efficient shift-invariant filtered-backprojection type), and (b) they required a very large detector, which is not practical to manufacture, or, equivalently, suffered from the so-called "long object problem", which means that objects extending outside the detector (axially truncated), which is common in human scans, cannot be reconstructed.

The exact line plus circle reconstruction method of Katsevich includes: shift invariant (convolution performed independently of reconstructed object, without pixel-dependency), and filtered backprojection (FBP) for both circle and line data.

However, the exact method of Katsevich algorithm may not be easily adapted to the hardware of existing medical CT scanners because it requires that a Hilbert convolution be applied in the frequency domain, and the Hilbert convolution requires a differentiation to be performed on the sensed data, which may cause degradation of spatial resolution. In addition, the Hilbert transform requires rebinning, which causes a considerable reduction in computational efficiency and some reduction of resolution. Thus, the application of such an algorithm for both circle and line data may be time consuming or require additional costly processing resources, and is also not suitable for commercial CT scanners.

SUMMARY OF THE INVENTION

One object of the present invention is to improve the quality of reconstructed images and remove cone beam artifacts. In the next section we describe a method to combine circle with line scan to remove the cone beam artifact.

Accordingly, to overcome the problems of the reconstruction algorithms of the related art, the present invention provides a method, system apparatus, and computer program product.

One object of this invention is to provide a novel volume image reconstruction apparatus, comprising: a data collection unit configured to receive circle projection data collected by a detector along a circular path with respect to an object, produce pre-processed circle projection data from the received circle projection data, receive line projection data collected by the detector along a linear path with respect to the object, and produce pre-processed line projection data from the received line projection data; a circle projection data reconstruction unit configured to produce a reconstructed circle path volume image of the object from the pre-processed circle projection data using a reconstruction algorithm that includes a ramp filter; a line projection data reconstruction unit configured to produce a reconstructed line path volume image of the object from the pre-processed line projection data using a reconstruction algorithm that includes a Hilbert filter; and an image volume processing unit configured to combine the reconstructed circle path volume image and the reconstructed line path volume image to produce the volume image of the object.

Another object of this invention is to provide a novel apparatus, wherein the linear path is not perpendicular to the plane of the circular path.

Another object of this invention is to provide a novel apparatus, wherein the circle projection data reconstruction unit comprises a backprojecting unit and a directional filtering unit, the backprojecting unit configured to produce the reconstructed circle path volume image based on filtered detector-space data, and the directional filtering unit comprises: a resampling section configured to resample the pre-processed circle projection data onto filtering curves representing pre-specified filtering directions to produce rebinned data; a filtering section configured to filter the rebinned data along the filtering curves with the ramp filter to produce filtered data; and an inverse rebinning section configured to inverse rebin the filtered data to a detector grid to produce the filtered detector-space data.

Another object of this invention is to provide a novel apparatus, wherein the circle projection data reconstruction unit comprises: a pre-weighting section configured to pre-weight the pre-processed circle projection data by a cosine of a fan angle of the detector and a cosine of a cone angle of the detector to obtain pre-weighted data; a filtering section configured to filter the pre-weighted data with a Feldkamp, Davis, Kress (FDK) ramp filter along rows of the detector or along pre-specified filtering curves to produce filtered data, and a backprojecting section configured to backproject the filtered data to produce the reconstructed circle path volume image.

Another object of this invention is to provide a novel apparatus, wherein the circle projection data reconstruction unit comprises: a pre-weighting section configured to pre-weight the pre-processed data by a cosine of a cone angle of the detector to obtain pre-weighted data; a hybrid filtering section configured to filter the pre-weighted data with a Zamyatin, Taguchi, Silver (ZTS) ramp filter along rows of the detector or along pre-specified filtering curves to produce filtered data, and a backprojecting unit configured to backproject the filtered data to produce the reconstructed circle path volume image.

Another object of this invention is to provide a novel apparatus, wherein the data collection unit is further configured to receive circle projection data collected by the detector along the circular path comprising a portion of a full circle, and produce the pre-processed circle data having different weighting for singly-measured and doubly measured rays in the received circle projection data.

Another object of this invention is to provide a novel apparatus, wherein the line projection data reconstruction unit comprises: a differentiator configured to calculate a derivative of the detected line projection data to produce derivative data; a rebinning section configured to rebin the derivative data onto filtering curves to produce rebinned data; a Hilbert filtering section configured to Hilbert filter the rebinned data along the filtering curves to produce filtered data; an inverse rebinning section configured to inverse rebin the filtered data to a detector grid to produce filtered detector-space data; and a backprojecting unit configured to backproject the filtered detector-space data to produce the reconstructed line path volume image.

Another object of this invention is to provide a novel apparatus, wherein the line projection data reconstruction unit comprises: a downsampling section configured to downsample the pre-processed line projection data by a sampling factor selected from 2, 3, 4, or 5 to produce downsampled data; a differentiator configured to calculate a derivative of the downsampled data to produce derivative data; a rebinning section configured to rebin the derivative data onto filtering curves to produce rebinned data; a Hilbert filtering section configured to Hilbert filter the rebinned data along the filtering curves to produce filtered data; an inverse rebinning section configured to inverse rebin the filtered data to a detector grid to produce filtered detector-space data; a backprojecting unit configured to backproject the filtered detector-space data to produce a downsampled line path volume image; and an upsampling unit configured to upsample the downsampled line path volume image by the sampling factor to produce the reconstructed line path volume image.

Another object of this invention is to provide a novel apparatus, further comprising: an x-ray tube configured to expose the object to a radiation corresponding to an electric current in the x-ray tube, and the electric current is less than or equal to 20 mA; and a detector configured to produce the line projection data when the object is exposed to the radiation.

Another object of this invention is to provide a novel apparatus, further comprising: a couch inaccuracy compensating unit configured to adjust a reconstruction parameter based on a correlation between the pre-processed circle projection data and the pre-processed line projection data, and the line projection data reconstruction unit is further configured to produce the reconstructed line path volume image of the object based on the reconstruction parameter.

Another object of this invention is to provide a novel apparatus, wherein the line projection data reconstruction unit comprises: a differentiator configured to calculate a derivative of the detected line projection data to produce derivative data; a rebinning section configured to rebin the derivative data onto filtering curves to produce rebinned data; a Hilbert filtering section configured to Hilbert filter the rebinned data along the filtering curves to produce filtered data; and a backprojecting unit configured to backproject the filtered data directly from the filtering curves to produce the reconstructed line path volume image.

Another object of this invention is to provide a novel apparatus, further comprising: a source configured to controllably expose the object to a radiation; a detector configured to produce the line projection data when the object is exposed to the radiation; and an active collimation unit configured to control the source to expose the object to the radiation with an exposure aperture that corresponds to a part of the detector that receives data to be filtered by a filtering unit.

Another object of this invention is to provide a novel apparatus, wherein the data collection unit is further configured to receive the circle projection data collected by the detector along plural portions of the circular path at different capture times and produce plural pre-processed circle projection data each corresponding to a different capture time, and the image volume processing unit is further configured to produce plural volume images of the object based on the plural pre-processed circle projection data, the apparatus further comprising: an aggregating unit configured to aggregate the plural volume images of the object from the image volume processing unit and produce aggregated data of the plural volume images; and a compositing unit configured to produce a composite volume image of the object from the aggregated data of the plural volume images.

Another object of this invention is to provide a novel apparatus, wherein the object exhibits repeated phases, the apparatus further comprising: an object repetitive mode determining unit configured to identify a phase time when the object exhibits a phase of interest in the repeated phases; and the compositing unit is further configured to produce the composite volume image based on at least one of the plural volume images corresponding to the phase time when the object exhibits the phase of interest.

Another object of this invention is to provide a novel apparatus, wherein the object exhibits repeated phases, the apparatus further comprising: an object repetitive mode determining unit configured to identify a phase time when the object exhibits a phase of interest in the repeated phases; and the data collection unit is further configured to receive the circle projection data collected by the detector along plural portions of the circular path at different capture times and produce plural pre-processed circle projection data each corresponding to a different capture time, and produce the pre-processed circle projection data from the plural pre-processed circle projection data corresponding to the time interval when the object exhibits the phase of interest.

Another object of this invention is to provide a novel apparatus, wherein the data collection unit is further configured to receive the circle projection data collected by the detector along plural circular paths and produce plural pre-processed circle projections each corresponding to a different circle path in the plural circular paths, the image volume processing unit is further configured to produce plural volume images of portions of the object based on plural reconstructed circle path volume images each corresponding to one of the plural pre-processed circle projections, and combine the plural volume images of the portions of the object to produce the volume image of the object.

Another object of this invention is to provide a novel method of reconstructing a volume image of an object, the method comprising: receiving circle projection data collected by a detector along a circular path with respect to the object; producing pre-processed circle projection data from the received circle projection data; receiving line projection data collected by the detector along a linear path with respect to the object; producing pre-processed line projection data from the received line projection data; producing a reconstructed circle path volume image of the object from the pre-processed circle projection data using a reconstruction algorithm that includes a ramp filter; producing a reconstructed line path volume image of the object from the pre-processed line projection data using a reconstruction algorithm that includes a Hilbert filter; and combining the reconstructed circle path volume image and the reconstructed line path volume image to produce the volume image of the object.

Another object of this invention is to provide a novel method, wherein the linear path is not perpendicular to the plane of the circular path.

Another object of this invention is to provide a novel method, wherein the producing the reconstructed circle path volume image further comprises: resampling the pre-processed circle projection data onto filtering curves representing pre-specified filtering directions to produce rebinned data; filtering the rebinned data along the filtering curves with the ramp filter to produce filtered data; inverse rebinning the filtered data to a detector grid to produce the filtered detector-space data; and backprojecting the filtered detector-space data to produce the reconstructed circle path volume image.

Another object of this invention is to provide a novel method, wherein the producing the reconstructed circle path volume image further comprises: pre-weighting the pre-processed circle projection data by a cosine of a fan angle of the detector and a cosine of a cone angle of the detector to obtain pre-weighted data; filtering the pre-weighted data with a Feldkamp, Davis, Kress (FDK) ramp filter along rows of the detector or along pre-specified filtering curves to produce filtered data, and backprojecting the filtered data to produce the reconstructed circle path volume image.

Another object of this invention is to provide a novel method, wherein the producing the reconstructed circle path volume image further comprises: pre-weighting the pre-processed data by a cosine of a cone angle of the detector to obtain pre-weighted data; hybrid filtering the pre-weighted data with a Zamyatin, Taguchi, Silver (ZTS) ramp filter along rows of the detector or along pre-specified filtering curves to produce filtered data, and backprojecting the filtered data to produce the reconstructed circle path volume image.

Another object of this invention is to provide a novel method, wherein: the receiving the circle projection data receives the circle projection data collected by the detector along the circular path comprising a portion of a full circle; and the producing the pre-processed circle projection data produces the pre-processed circle data having different weighting for singly-measured and doubly measured rays in the received circle projection data.

Another object of this invention is to provide a novel method, wherein the producing the reconstructed line path volume image further comprises: calculating a derivative of the detected line projection data to produce derivative data; rebinning the derivative data onto filtering curves to produce rebinned data; Hilbert filtering the rebinned data along the filtering curves to produce filtered data; inverse rebinning the filtered data to a detector grid to produce filtered detector-space data; and backprojecting the filtered detector-space data to produce the reconstructed line path volume image.

Another object of this invention is to provide a novel method, further comprising: downsampling the pre-processed line projection data by a sampling factor selected from 2, 3, 4, or 5 to produce downsampled data; calculating a derivative of the downsampled data to produce derivative data; rebinning the derivative data onto filtering curves to produce rebinned data; Hilbert filtering the rebinned data along the filtering curves to produce filtered data; inverse rebinning the filtered data to a detector grid to produce filtered detector-space data; backprojecting the filtered detector-space data to produce a downsampled line path volume image; and upsampling the downsampled line path volume image by the sampling factor to produce the reconstructed line path volume image.

Another object of this invention is to provide a novel method, further comprising: exposing the object to a radiation corresponding to an electric current in an x-ray tube, and the electric current is less than or equal to 20 mA; and producing the line projection data when the object is exposed to the radiation.

Another object of this invention is to provide a novel method, further comprising: compensating a couch inaccuracy by adjusting a reconstruction parameter based on a correlation between the pre-processed circle projection data and the pre-processed line projection data; and producing the reconstructed line path volume image of the object based on the reconstruction parameter.

Another object of this invention is to provide a novel method, wherein the producing the line path volume image further comprises: calculating a derivative of the detected line projection data to produce derivative data; a rebinning section configured to rebin the derivative data onto filtering curves to produce rebinned data; a Hilbert filtering section configured to Hilbert filter the rebinned data along the filtering curves to produce filtered data; and a backprojecting unit configured to backproject the filtered data directly from the filtering curves to produce the reconstructed line path volume image.

Another object of this invention is to provide a novel method, further comprising: controllably exposing the object to a radiation; producing the line projection data when the object is exposed to the radiation; and controlling the exposing to expose the object to the radiation with an exposure aperture that corresponds to a part of the detector that receives data to be filtered by a filtering unit.

Another object of this invention is to provide a novel method, wherein the receiving the circle projection data receives the circle projection data collected by the detector along plural portions of the circular path at different capture times, the producing the pre-processed circle projection data produces plural pre-processed circle projection data each corresponding to a different capture time, and the combining produces plural volume images of the object based on the plural pre-processed circle projection data, the method further comprising: aggregating the plural volume images of the object; producing aggregated data of the plural volume images; and producing a composite volume image of the object from the aggregated data of the plural volume images.

Another object of this invention is to provide a novel method, wherein the object exhibits repeated phases, the method further comprising: identifying a phase time when the object exhibits a phase of interest in the repeated phases; and producing the composite volume image based on at least one of the plural volume images corresponding to the phase time when the object exhibits the phase of interest.

Another object of this invention is to provide a novel method, wherein the object exhibits repeated phases, the method further comprising: identifying a phase time when the object exhibits a phase of interest in the repeated phases; receiving the circle projection data collected by the detector along plural portions of the circular path at different capture times; producing plural pre-processed circle projection data each corresponding to a different capture time; and producing the pre-processed circle projection data from the plural pre-processed circle projection data corresponding to the time interval when the object exhibits the phase of interest.

Another object of this invention is to provide a novel method, wherein: the receiving the circle projection data receives the circle projection data collected by the detector along plural circular paths; the producing the pre-processed circle projection data produces plural pre-processed circle projections each corresponding to a different circle path in the plural circular paths; producing plural volume images of portions of the object based on plural reconstructed circle path volume images each corresponding to one of the plural pre-processed circle projections; and the combining combines the plural volume images of the portions of the object to produce the volume image of the object.

Another object of this invention is to provide a novel computer-readable medium storing computer program instructions, which when executed by a computer, cause the computer to perform steps comprising: receiving circle projection data collected by a detector along a circular path with respect to an object; producing pre-processed circle projection data from the received circle projection data; receiving line projection data collected by the detector along a linear path with respect to the object; producing pre-processed line projection data from the received line projection data; producing a reconstructed circle path volume image of the object from the pre-processed circle projection data using a reconstruction algorithm that includes a ramp filter; producing a reconstructed line path volume image of the object from the pre-processed line projection data using a reconstruction algorithm that includes a Hilbert filter; and combining the reconstructed circle path volume image and the reconstructed line path volume image to produce a volume image of the object.

To minimize impact and cost associated with hardware development, the present invention includes ramp-based reconstruction of the circle data, which may be implemented with minimal changes to existing equipment. In addition, as ramp filter based reconstruction algorithms (e.g., FDK or a Zamyatin, Taguchi, Silver (ZTS) ramp filter based) may be commonly used by conventional CT medical imaging devices, there are established libraries of ramp functions each of which have been prepared for a particular application based on the body part to be imaged. Thus, the present invention may advantageously utilize ramp functions from this existing library of ramp functions to avoid uncertainty and cost that would be associated with the development of application specific filter functions in a different approach (e.g., body part specific filtering approaches for a Hilbert function based approach).

The line data provides an additional term that cancels the cone beam artifacts due to incomplete circular trajectory.

The present approach has been proven feasible based on simulated data and real scanned data of the anthropomorphic phantom. The present approach has been proven stable with respect to contrast injection, patient motion, and misalignments during the scan. The additional dose to which a patient is exposed resulting from the line scan is also advantageously relatively low compared to that of the circle scan. The present invention also allows cone beam artifact-free reconstruction even when the cone angle is very large, and can be used when the number of detector rows exceeds 256.

According to an embodiment of the present invention, ramp-filter based reconstruction (such as FDK or ZTS, for example) of the circle data is performed, in addition to a low-dose line scan, which is reconstructed using a method including the Hilbert transform. Also, the line data may be down-sampled by a factor of 2 to 4, to accelerate reconstruction, and to obtain additional performance improvements (e.g., reduced memory and processing capacity). Thus, the present invention is suitable for commercial CT scanners.

Some clinical applications require a gantry tilt, which causes the line segment to be tilted relative to the circular trajectory. In other words, the line segment is not perpendicular to the plane of the circle trajectory. Thus, an embodiment of the invention pertains to a case where the gantry is tilted, for example during brain imaging, where the gantry is tilted before the scan so that reconstruction planes are parallel to the orbitomeatal (OM) line that connects the patient's eye with the center of the patient's ear. The plane that contains OM line serves as the reference anatomical plane. Also, tilting the gantry helps to minimize the exposure to the eye lenses of the patient.

Other methods, systems, and computer program products of the present invention will become apparent to one or ordinary skill in the art upon examination of the following drawings and detailed description of the preferred embodiments.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 6 is a flow chart of a method of performing reconstruction of a line volume image according to an embodiment of the present invention;

FIG. 20A is a view of a FOV in a method of reducing an exposure dose of the line scan using line scan collimation according to an embodiment of the present invention;

FIG. 20B is another view of a FOV in a method of reducing an exposure dose of the line scan using line scan collimation according to an embodiment of the present invention;

FIG. 20C is another view of a FOV in a method of reducing an exposure dose of the line scan using line scan collimation according to an embodiment of the present invention;

FIG. 20D is another view of a FOV in a method of reducing an exposure dose of the line scan using line scan collimation according to an embodiment of the present invention;

FIG. 20E is another view of a FOV in a method of reducing an exposure dose of the line scan using line scan collimation according to an embodiment of the present invention;

FIG. 20F is another view of a FOV in a method of reducing an exposure dose of the line scan using line scan collimation according to an embodiment of the present invention;

FIG. 28A is an example of expanding a reconstructed volume of interest (VOI) according to an embodiment of the invention;

FIG. 28B is a line view of the shapes of FDK VOI Extended FDK VOI;

FIG. 29A is an example of combining data from plural circle scans with one or more line scans, according to another embodiment of the present invention;

FIG. 29B is an example of combining data from plural circle scans with one or more line scans, according to another embodiment of the present invention;

FIG. 29C is an example of combining data from plural circle scans with one or more line scans, according to another embodiment of the present invention;

FIG. 29D is an example of combining data from plural circle scans with one or more line scans, according to another embodiment of the present invention;

FIG. 29E is an example of combining data from plural circle scans with one or more line scans, according to another embodiment of the present invention; and FIG. 29F is an example of combining data from plural circle scans with one or more line scans, according to another embodiment of the present invention.

DETAILED DESCRIPTION OF THE PREFERRED EMBODIMENTS

Figure 1:
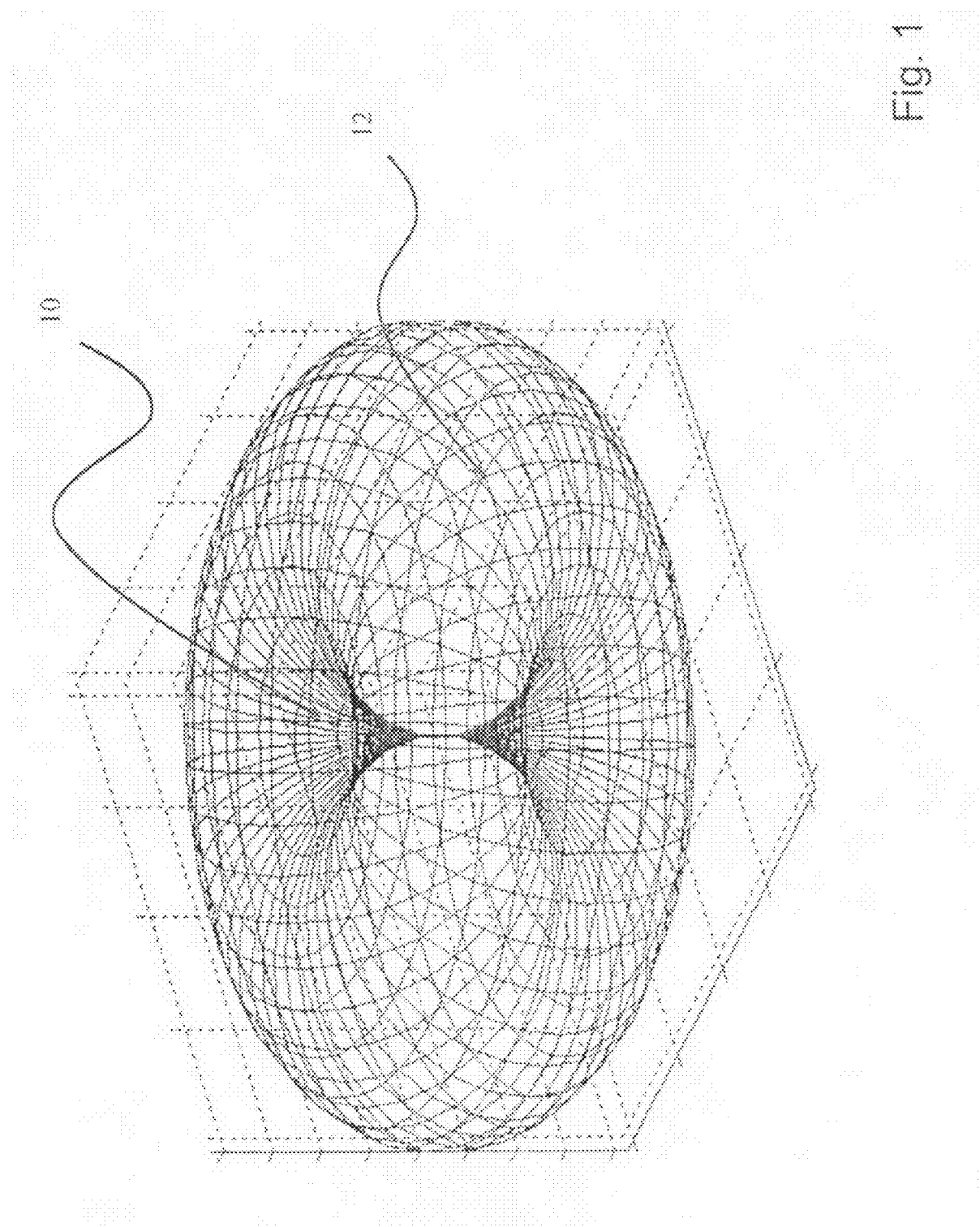
FIG. 1 is a graph of an example of circular data coverage in the Radon space.
Figure 2:
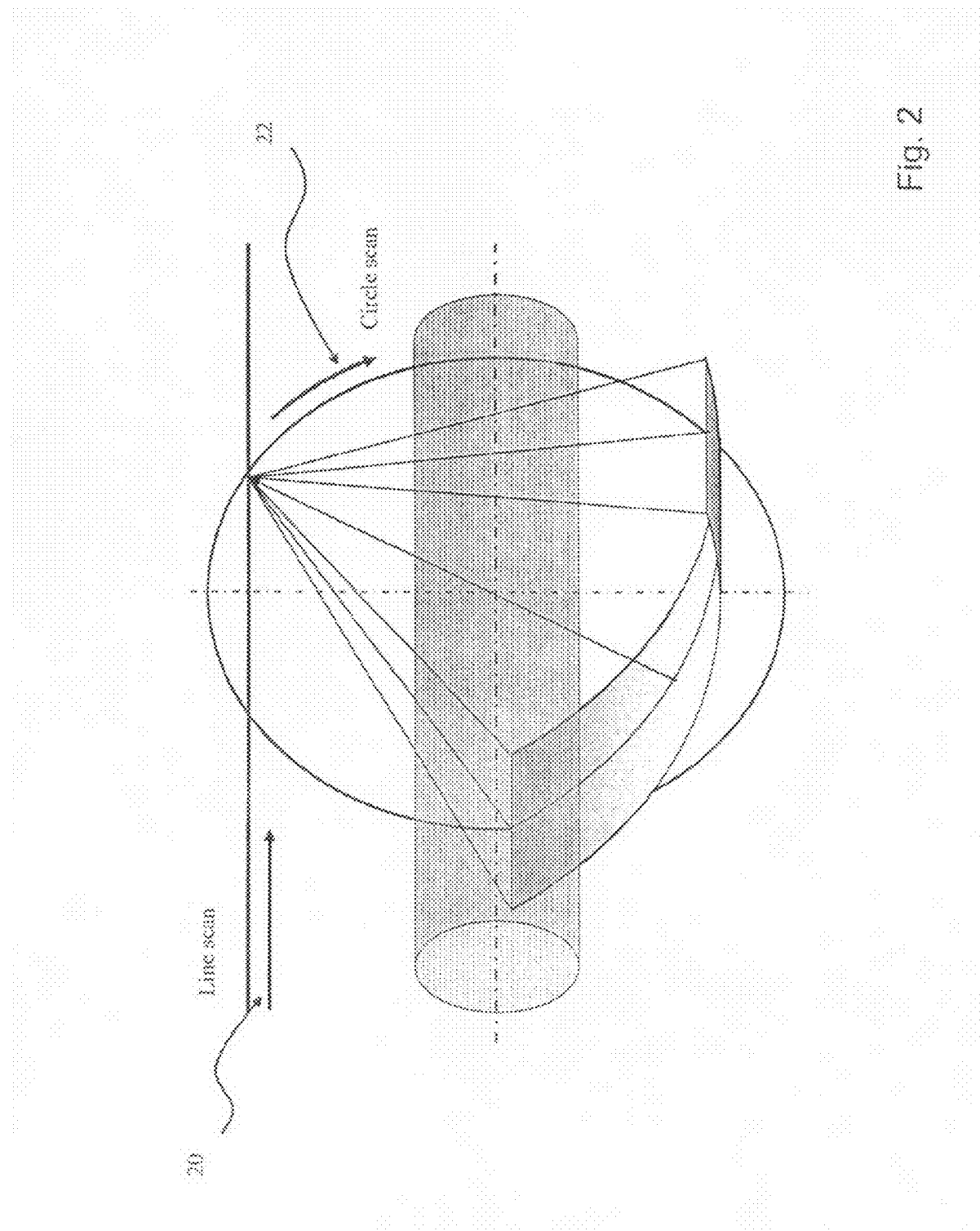
FIG. 2 is an isometric view of an example of a relationship between a line scan trajectory and a circle scan trajectory.
Figure 3:
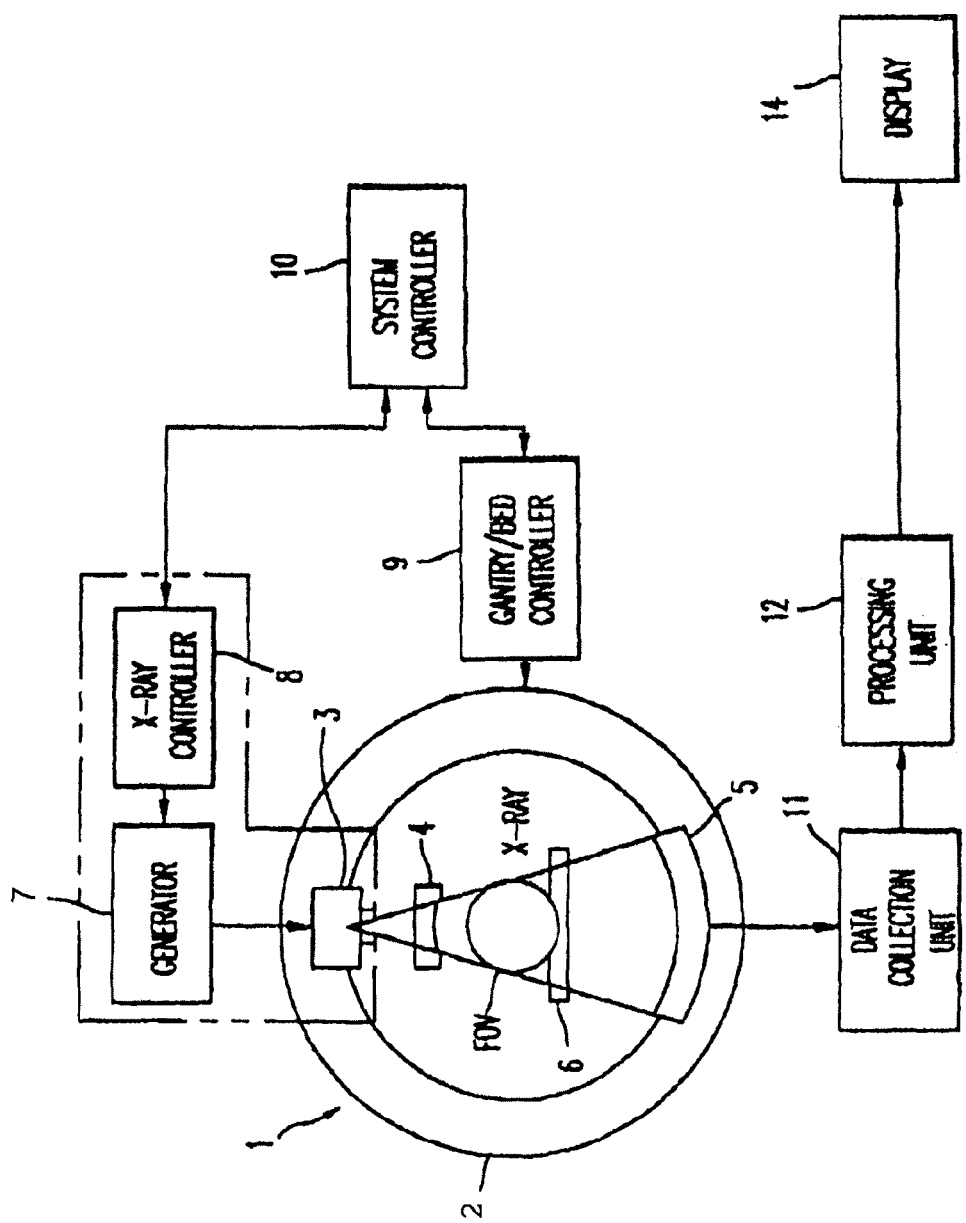
FIG. 3 is a block diagram of an embodiment of the present invention.

Referring now to the drawings, wherein like reference numerals designate identical or corresponding parts throughout the several views, and more particularly to FIG. 3 thereof, which is a block diagram of an embodiment of an x-ray computed tomography imaging apparatus according to the present invention. The imaging apparatus includes gantry 1 having an x-ray source 3 that generates a cone-beam of x-ray flux approximately cone-shaped, and a two-dimensional array type x-ray detector 5 including a plurality of detector elements arranged in two-dimensional fashion, i.e., a plurality of elements arranged in one dimension stacked in a plurality of rows. X-ray source 3 and two-dimensional array type x-ray detector 5 are installed on a rotating ring 2 and facing opposite sides of a subject, who is laid on a sliding bed 6. Two-dimensional array type x-ray detector 5 is mounted on the rotating ring 2. Each detector element corresponds to one channel of sensed data. X-rays from x-ray source 3 are directed on to subject through an x-ray filter 4. X-rays that pass through the subject are detected as an electrical signal by the two-dimensional array type x-ray detector 5.

X-ray controller 8 supplies a trigger signal to high voltage generator 7. High voltage generator 7 applies high voltage to x-ray source 3 according to a timing with which the trigger signal is received and causing x-rays to be emitted from x-ray source 3. Gantry/bed controller 9 synchronously controls the revolution of rotating ring 2 of gantry 1 and the sliding of the sliding sheet of bed 6. System controller 10 constitutes the control center of the entire system and controls x-ray controller 8 and gantry/bed controller 9 such that, as seen from the subject, x-ray source 3 executes circle scans and line scans.

During a circle scan according to the present embodiment, rotating ring 2 (including the source 3 and the detector 5) is continuously rotated with a fixed angular speed while the sliding bed 6 remains in a fixed position, and x-rays are emitted continuously or intermittently at fixed angular intervals from x-ray source 3. Thus, as the bed 6 remains stationary, the circle detector 5 moves along a true circular path with respect to the object being scanned, and does not move in a helical path. During a line scan, the bed 6 is moved linearly through the gantry with a fixed speed while x-rays are emitted continuously or intermittently from x-ray source 3, which is held in a stationary position, for example directly over the bed 6.

In the embodiment of the linear scan described above, the patient or object to be imaged is moved through the gantry while the source and detector are held in a fixed position. However, the invention also includes embodiments in which the object is held in a fixed position and the detector moves along the object, as well as embodiments in which both the object and the detector move. The circle scan and the line scan are performed one after the other, in any order.

In the embodiment of circular scanning described above, the path of the detector 5 is indicated as being circular. However, the invention is not limited to circular paths but also includes other curved paths around the object.

The output signal of two-dimensional array type x-ray detector 5 is amplified by a data collection unit 11 for each channel and converted to a digital signal, to produce projection data, and in particular to produce line projection data, during a line scan, and circle projection data during a circle scan. The projection data is pre-processed using methods known to one of skill in the art, and the pre-processed data is output from data collection unit 11 to reconstruction processing unit 12. Reconstruction processing unit 12 uses the pre-processed data to produce a volume image of the object being scanned.

The reconstructed volume image may be sent to display device 14, where it is displayed visually as a three-dimensional image or tomographic image.

For the purposes of this description we shall define a volume image to be a representation of the physical object being scanned, in which the image has been generated by some imaging technology. Examples of imaging technology could include television or CCD cameras or X-ray, sonar or ultrasound imaging devices. The initial medium on which an image is recorded could be an electronic solid-state device, a photographic film, or some other device such as a photostimulable phosphor. That recorded image could then be converted into digital form by a combination of electronic (as in the case of a CCD signal) or mechanical/optical means (as in the case of digitizing a photographic film or digitizing the data from a photostimulable phosphor).

A detector 5 used in the present embodiment may include a 256-detector row medical CT scanner detector [1-4], which has 120-millimeter volume coverage. One of skill in the art would also recognize that the present invention also applies to other conventional CT scanner detectors. Additional scanner parameters according to the present embodiment are shown in Table 1.

TABLE 1

| Scanner parameters | |
|---|---|
| Number of detector rows | 256 |
| Number of detector channels | 896 |
| Detector row height | 0.5 mm |
| Number of projections per rotation | 900 |
| Full fan angle | 49.2° |
| Field of view | 320 mm |
| Full cone angle | 12.18° |
| Line view pitch | 0.3 mm |
| Tube voltage | 120 kVp |
| Tube current for circle scan | 200 mA |
| Tube current for line scan | 50 mA |
| Rotation speed | 0.5 sec/rot |

Figure 4:
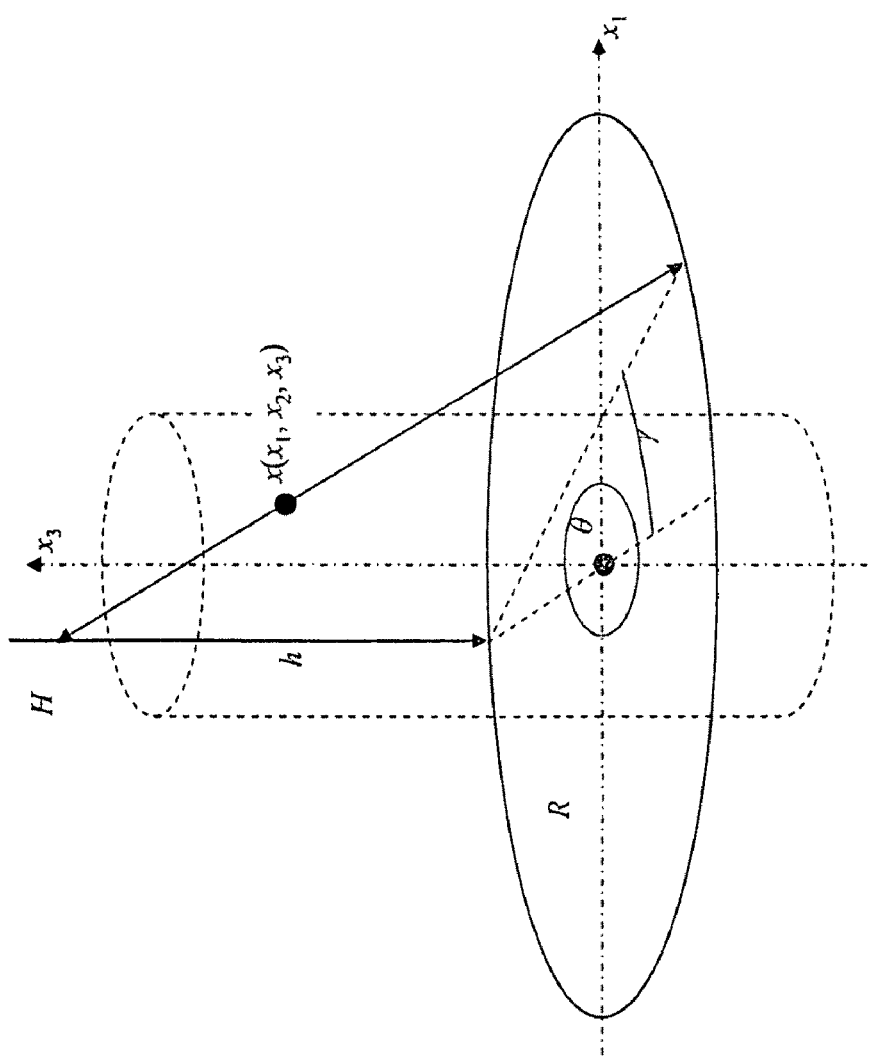
FIG. 4 is a block diagram of a physical coordinate system according to an embodiment of the present invention.

FIG. 4 is a block diagram of an example of a definition of a physical coordinate system of the imaging apparatus. Circle source position is given by $y_C(\beta)=(R \cos \beta, R \sin \beta, 0)$, where R is the radius of circle trajectory and $\beta$ is the view angle; line source position is given by $y_L(h)=(R \cos \theta, R \sin \theta, h)$, where $\theta$ is the fixed line angle and h is the line source vertical coordinate along the z-axis. An equation for a conventional exact algorithm [11] consists of a sum of two integral terms that correspond to integrals of circle and line data, respectively, as shown in equation (1):

$$f(x) = \int_C \frac{1}{\|\gamma(\beta)-x\|} H_{sin\gamma}^{D1}\left[\left(\frac{\partial}{\partial \beta}+\frac{\partial}{\partial \gamma}\right)g(\beta,\gamma,v)\right]d\beta + \int_L \frac{1}{\|\gamma(h)-x\|} H_{sin\gamma}^{D2}\left[\frac{\partial}{\partial h}g(h,\gamma,v)\right]dh, \quad (1)$$

In equation (1), x is the reconstruction point, $\gamma$ is the fan angle, v is the vertical detector coordinate. $H_{sin\gamma}^{Di}$, i=1, 2, is the 1-dimensional directional Hilbert filter, with kernel 1/sin ($\gamma$). Note that the filtering directions for line and circle scans are different.

On the other hand, according to the present invention, the exact algorithm of equation (1) is simplified. First, it can be shown that filtering directions on the curved detector are almost horizontal for the circle data (they are exactly horizontal on the flat detector). Therefore, according to the present invention, rebinning is not applied for the circle data. Secondly, it has been suggested [12] that the Hilbert convolution applied to the $\gamma$-derivative can be replaced by the ramp convolution. However, the present invention goes further and replaces the whole first term in equation (1) by the FDK reconstruction to not only improve speed and efficiency, but also improve resolution compared to Hilbert reconstruction (see [12] for comparison).

According to the present invention, the circle scan data is reconstructed using a reconstruction algorithm having a ramp filter, such as an FDK reconstruction algorithm or a ZTS reconstruction algorithm. Further, according to the present invention, the line scan data is reconstructed for calculation of the low-frequency correction terms to supplement the reconstructed circle scan data.

Figure 5:
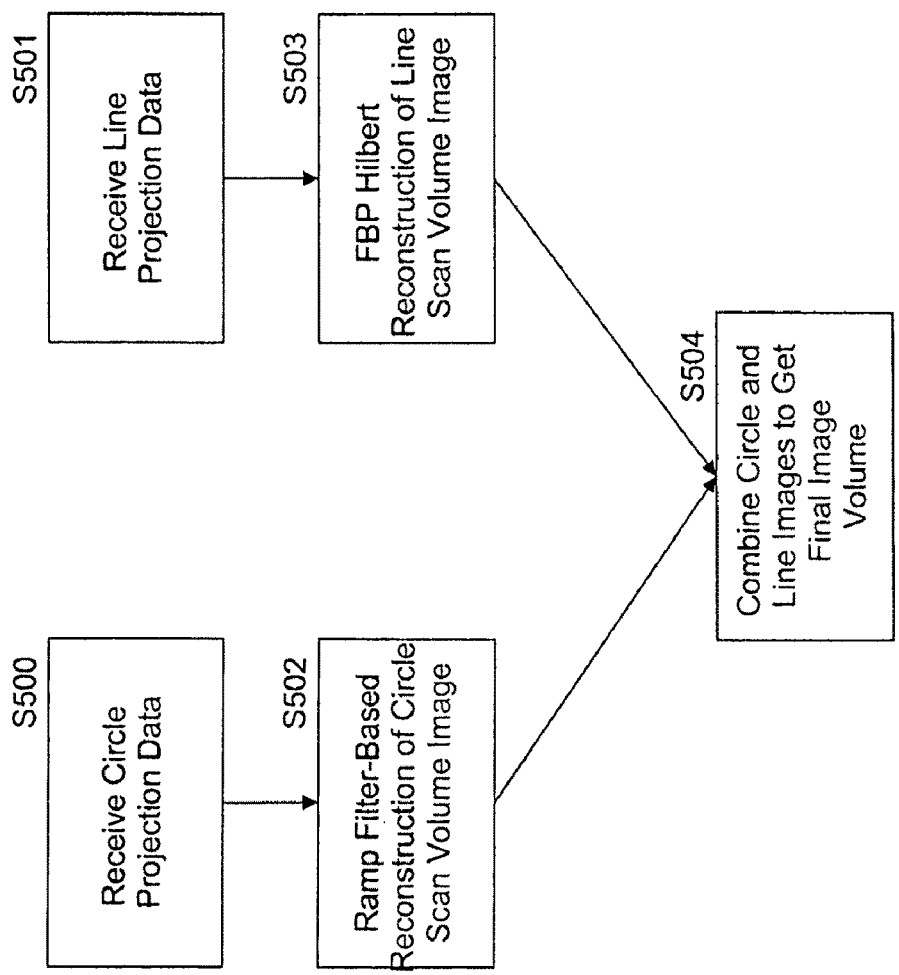
FIG. 5 is a flow chart of a method of performing image reconstruction according to an embodiment of the present invention.

FIG. 5 is a flow chart of a method of performing image reconstruction according to an embodiment of the present invention. In FIG. 5, the method includes step S500 in which preprocessed circle projection data is received, for example, from a preprocessor or detector including a preprocessor. In step S502, the received data is reconstructed to produce a circle projection volume image. In step S501, the preprocessed line scan projection data is received, and in step S503 the preprocessed line scan projection data is reconstructed using an filtered-backprojection (FBP) Hilbert reconstruction, to produce a line projection volume image. In step S504, the circle projection volume image and the line projection volume image are combined to produce the final and total volume image of the sensed object.

FIG. 6 is a flow chart of a method of performing reconstruction of a line volume image, for example performing step S503 in FIG. 5, according to the present invention. In FIG. 6, step S601 performs a differentiation of the received preprocessed line projection data. In step S602, the differentiated data is rebinned along filtering lines, in step S603, the rebinned data is filtered with a Hilbert filter along the filtering lines. In step S604, the Hilbert filtered data is rebinned back to the detector space or grid, in step S605, the rebinned data is 3D back-projected to produce the line projection volume image.

Figures 7A, 7B:
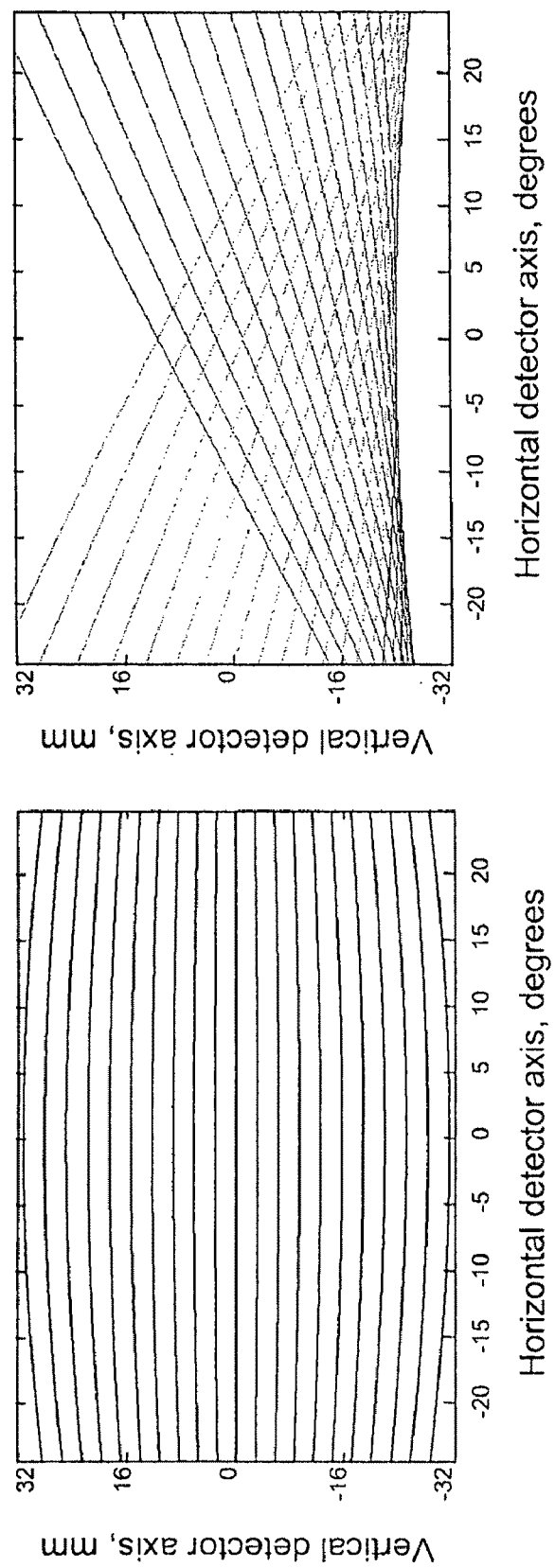
FIG. 7A is an example of filtering lines on the detector for data collected during a circular scan.
FIG. 7B is an example of filtering lines on the detector for data collected during a line scan.

FIG. 7A is an example of filtering lines on the detector for data collected during a circular scan. FIG. 7B is an example of filtering lines on the detector for data collected during a line scan. In the circle data, the filtering direction is almost horizontal, and for the line data, the filtering directions are tilted.

Convolution of the Line Data. First, let introduce the concept of PI-lines. Given a reconstruction pixel x, a PI-line is the line connecting some point on the circular trajectory and some point on the line trajectory and crossing the pixel x. It was shown in [11] that a PI-line can be found for each reconstruction pixel x. The PI-window (traced by the PI-lines between the line and circle parts of trajectory) on the flat detector is given by the parabola:

$$v_{fl} = -\frac{h}{2R^2}u^2 - \frac{h}{2},$$

where u and $v_{fl}$ are the horizontal and vertical flat detector coordinates, respectively. The vertex of the parabola is located at (0, −h/2). Using $\rho=\tan\gamma$ as a parameter of filtering lines, and taking into account that line $v_{fl}=mu+b$ on the flat detector is projected into the curve $v=b\cos\gamma+mR\sin\gamma$ on the curved detector [13], we obtain the following equations of the convolution lines, as shown in FIG. 7B (the vertical axis of FIG. 7B corresponds v, and the horizontal axis corresponds to γ):

$$v(\gamma, \rho, h) = -h\left(\frac{1-\rho^2}{2}\cos\gamma + \rho\sin\gamma\right) \quad (2)$$

The filtering family provides double coverage of the detector area. That is, for every pixel within the PI-window one can find two filtering lines through the pixel. In the full scan mode contributions from both lines are added; in the short scan mode only one sub-family is used.

Differentiation is performed in the direction of the source parameter (d/dh) and may be performed as a simple projection subtraction between two consecutive projections, divided by the linear distance between them. Alternatively, it can be implemented by a 3- or more point finite difference formula.

Further, rebinning to filtering lines may be performed as part of the Hilbert reconstruction of the line data. Note that rebinning is performed by resampling from Cartesian detector coordinates to non-Cartesian filtering coordinates. Usually that would require 2-dimensional interpolation; however, we apply resampling using only one-dimensional interpolation in the v-direction, and we keep sampling the same in the γ-direction.

Backprojection of the Line Data. Backprojection of the data can be performed directly from the filtering lines or directly from the filtering lines. Thus, only data within the PI-window is used (i.e., $v > v_\pi(\gamma)$., so that redundancy of the line data is taken into account. Another way is to apply the inverse rebinning to the detector coordinates; in this case line detector data should be masked by PI-window, given by equation (3):

$$v_\pi = -h/(2\cos\gamma). \quad (3)$$

Figure 8:
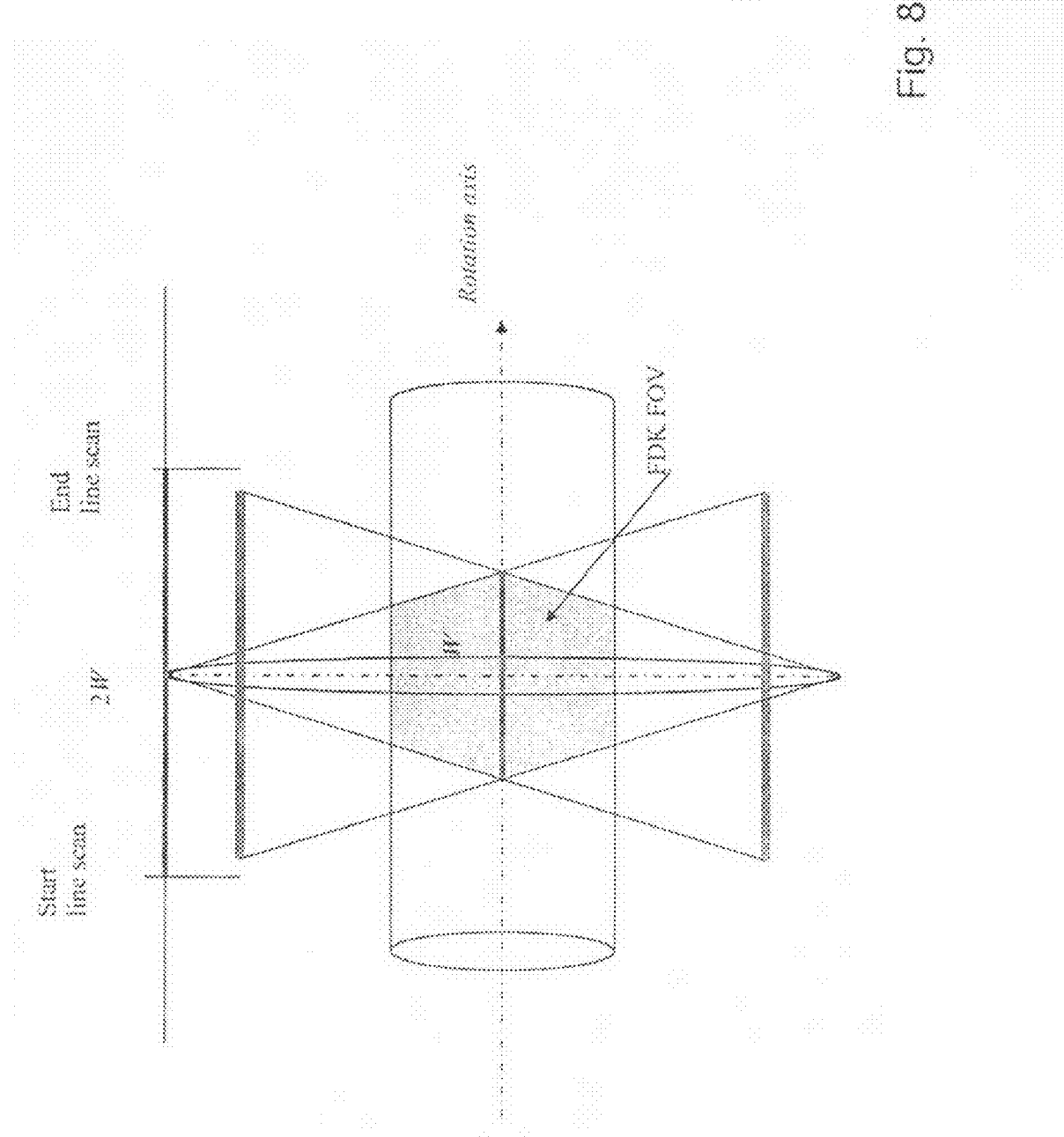
FIG. 8 is a block diagram of an example of the range of a line scan.

FIG. 8 is a block diagram of an example of the range of the line scan. Let W be the width of the detector at the isocenter. Then the required length of the line scan is 2W, i.e., the length of the line scan should be twice the detector size at the isocenter, or roughly the size of the physical detector. In this case, line data completely covers the hexagonal region that can be accurately reconstructed by FDK (shaded region in FIG. 8), i.e. the line data is sufficient for an exact reconstruction of the field of view according to a ramp filter based algorithm that includes a ramp based filter, such as the FDK filter or a ZTS filter [15] and [16].

Figure 9:
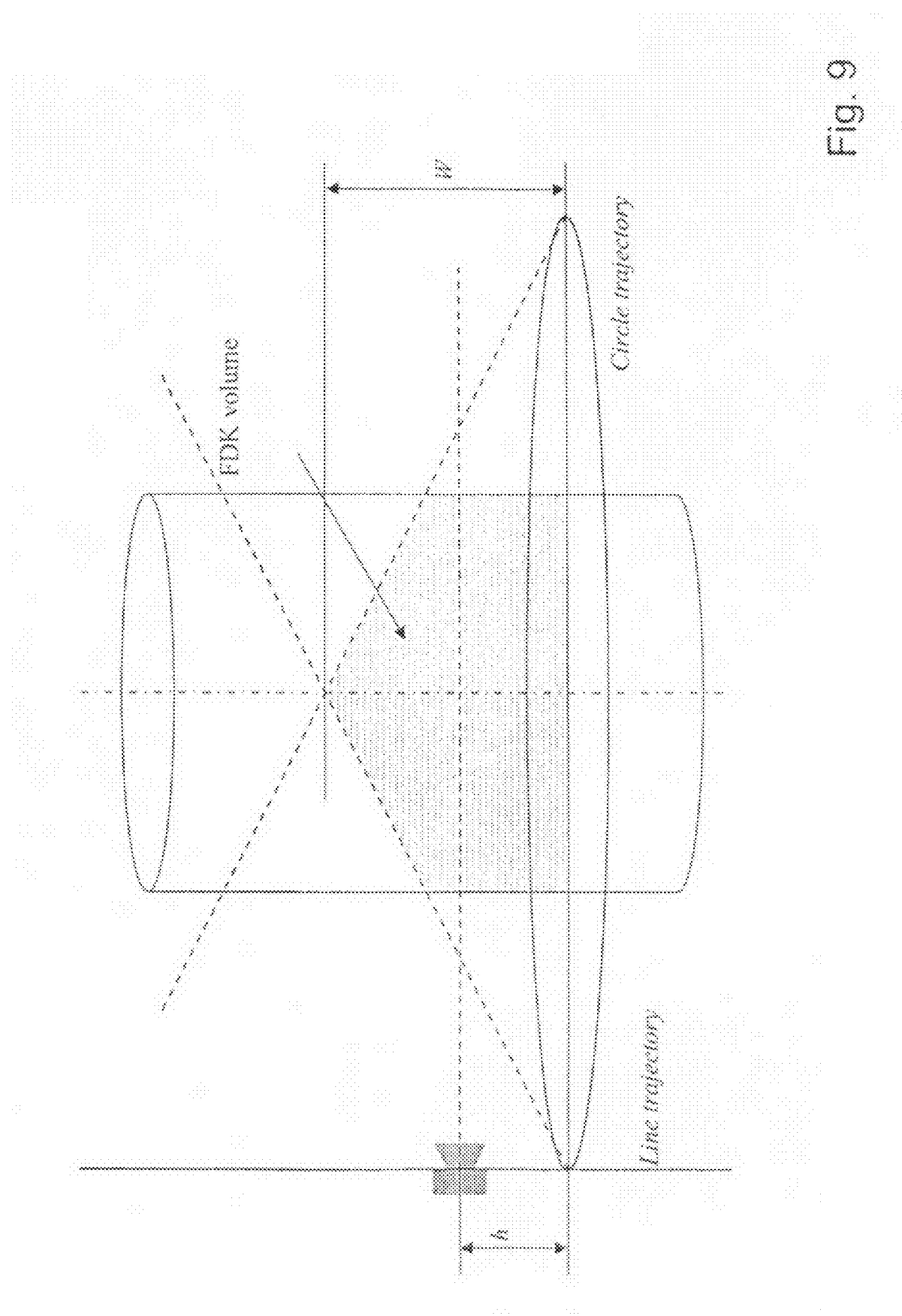
FIG. 9 is a block diagram with further nomenclature for considering the geometries of flat and curved detectors.

FIG. 9 is a block diagram with further nomenclature for considering the geometries of flat and curved detectors. W is the detector half-width (e.g., W=64 mm), H is line scan length in one direction, and h is the line source position, h<H. Here we only describe the case when h>0, and the case when h<0 may be treated similarly. (v, γ) are the cylindrical detector coordinates: v is the vertical coordinate, γ is the fan angle. (w, ρ) are the flat detector coordinates: w is the vertical coordinate, $w=v/\cos\gamma$. ρ is the horizontal coordinate, $\rho=\tan\gamma$. The vertical axis of each of FIGS. 7A and 7B corresponds to v, and the horizontal axis corresponds to γ.

Flat Detector. First, equations for the flat detector are shown, and then those equations are converted to apply to the cylindrical detector using the relationship indicating that a line on the flat detector $w=m\rho+b$ corresponds to the curve $v=b\cos\gamma+m\sin\gamma$ on the cylindrical detector.

Projection boundary of the PI window is given by equation (4):

$$w_{PI}(\rho, h) = -\frac{h}{2}(1+\rho^2). \quad (4)$$

According to the equation above, convolution lines on the flat detector are the tangent lines to the parabola $w_{PI}(\rho, h)$. The slope of the tangent line to a point (w, ρ) on the parabola is given by:

$$m = \frac{dw_{PI}}{d\rho} = h\rho \quad (5)$$

Thus, the equation of the line with the slope m through the point $(x_0, y_0)$ is given by:

$$y - y_0 = m(x - x_0) \quad (6)$$

For a given point $(w_0, \rho_0)$ on the parabola $w_{PI}(\rho, h)$, the slope of the tangent line through this point is $m=-h\rho_0$ and $w_0=-h(1+\rho_0^2)/2$. Then the equation of the tangent line through this point is: $w=-h(1+\rho_0^2)/2-h\rho_0(\rho-\rho_0)$. Working out this equation we obtain the equation of the tangent line on the flat detector:

$$w_\tau(\rho, h) = (-h\rho_0)\rho + \frac{h}{2}(\rho_0^2 - 1) \quad (7)$$

Next, the limits of $\rho_0$, namely $\rho_{min}$ and $\rho_{max}$, are selected such that filtering lines cover the whole BPJ area on the detector, in each of two cases: full scan and half scan.

In the full scan case, the filtering family is symmetric, that is, $\rho_{min}=-\rho_{max}$. Therefore, it is sufficient to find $\rho_{max}$. The parameter $\rho_{max}$ is determined by the filtering line that covers the peak point A of the FDK volume projection (critical case). Thus, coordinates of the point A are (ρ=0, w=W−h). Plugging in these coordinates into equation (7) we can find $\rho_0$ corresponding to $\rho_{max}$:

$$W - h = \frac{h}{2}(\rho_{max}^2 - 1) \quad (8)$$

From which is obtained:

$$\rho_{max} = \sqrt{\frac{2W}{h} - 1} = \sqrt{\rho_X}, \quad (9)$$
$$\rho_{min} = -\sqrt{\rho_X}$$

where $$\rho_X = \frac{2W}{h} - 1. \quad (10)$$

Equations (9)-(10) impose a restriction on the length of the line scan, H. The coordinate $\rho_X$ has to be nonnegative, which enforces the following condition: $h \leq 2W$. Therefore, for FDK-volume reconstruction the length of the line scan has to be exactly twice the detector extent, H=2W.

Figure 10:
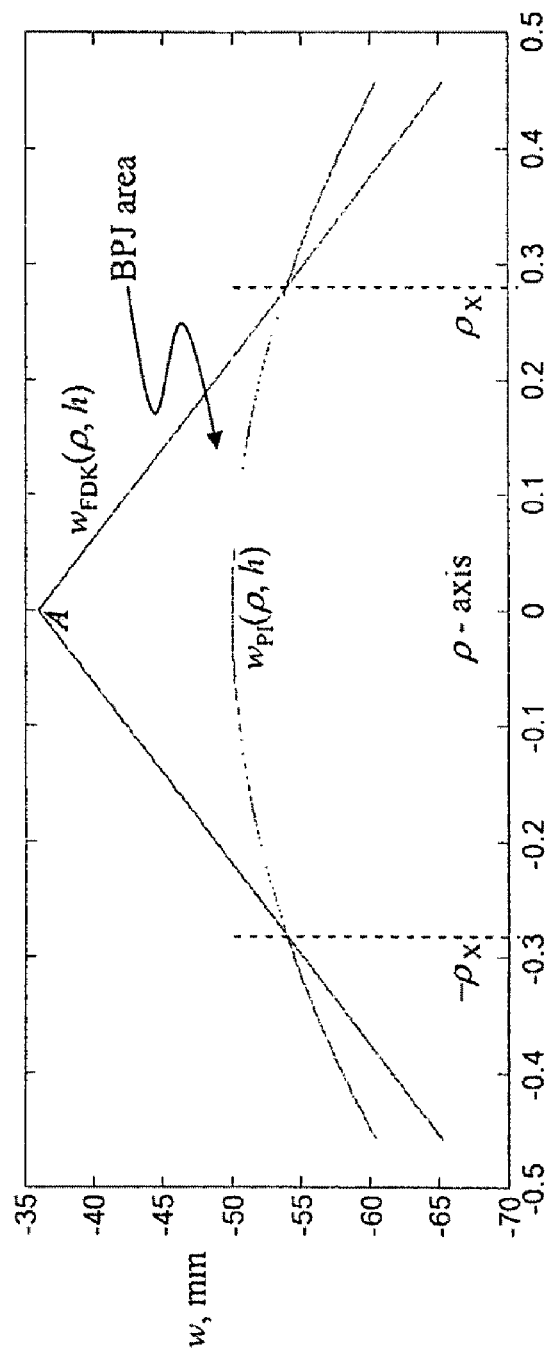
FIG. 10 is a plot of the BPJ area on a graph of w vs ρ according to an example of the present embodiment.

FIG. 10 is a plot of the BPJ area on a graph of w vs ρ according to an example of the present embodiment in which W=64 mm, h=100 mm, and $\rho_X$=0.28.

In the half scan case, the filtering family is not symmetric, since it should cover the BPJ are on only one side. If we cover the BPJ from the right, then $\rho_{max}$ is given by equation (10).

The parameter $\rho_{min}$ is determined by the BPJ area. Let $\rho_1 = \tan \gamma_{max}$. Then $$\rho_{min} = -\begin{cases} \rho_X, & \text{if } \rho_X \leq \rho_1 \\ \rho_1, & \text{if } \rho_X > \rho_1. \end{cases} \quad (11)$$

Projection boundary of the PI window is given by:

$$v_{PI}(\gamma, h) = -\frac{h}{2\cos\gamma}. \quad (12)$$

Convolution lines. From equation (7) we see that:

$$m = -h\rho \quad (13\text{-}14)$$
$$b = -\frac{h}{2}(1 - \rho^2)$$

(we now write "ρ" instead of "$\rho_0$" for simplicity), and we obtain the equations of the filtering curves on the flat detector:

$$v(\gamma, \rho, h) = -h\left(\frac{1-\rho^2}{2}\cos\gamma + \rho\sin\gamma\right) \quad (15)$$

Note that the filtering family on the cylindrical detector uses the same indexing parameter as the family on the flat detector. Therefore, we can use equations (10)-(11) to find limits for ρ.

Figure 11B:
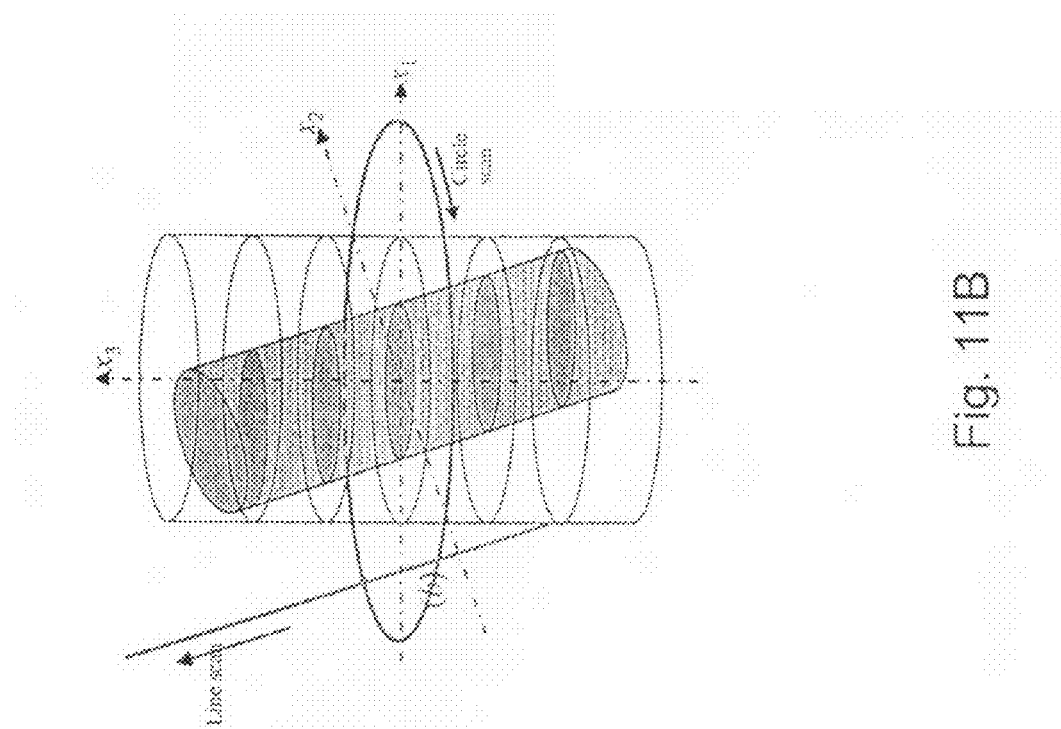
FIG. 11B is an isometric view of tilted coordinates associated with the circular trajectory.
Figure 11A:
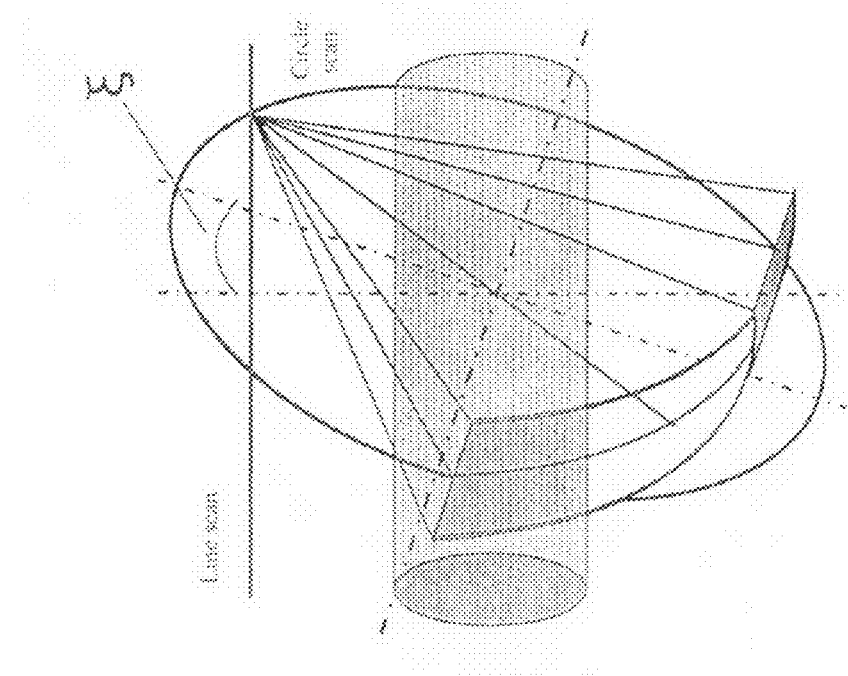
FIG. 11A is an isometric view of an embodiment of the present invention including a tilted gantry.

FIG. 11A is an isometric view of an embodiment of the present invention including a tilted gantry. FIG. 11B is an isometric view of tilted coordinates associated with the circular trajectory. In the tilted geometry the structure of the algorithm remains similar to the non-tilted case described above, and image reconstruction is performed in the tilted coordinate system, which implies that reconstruction of the circle data stays the same as without the gantry tilt. Therefore in this section we describe only the reconstruction from the line data in the tilted geometry.

Figure 12B:
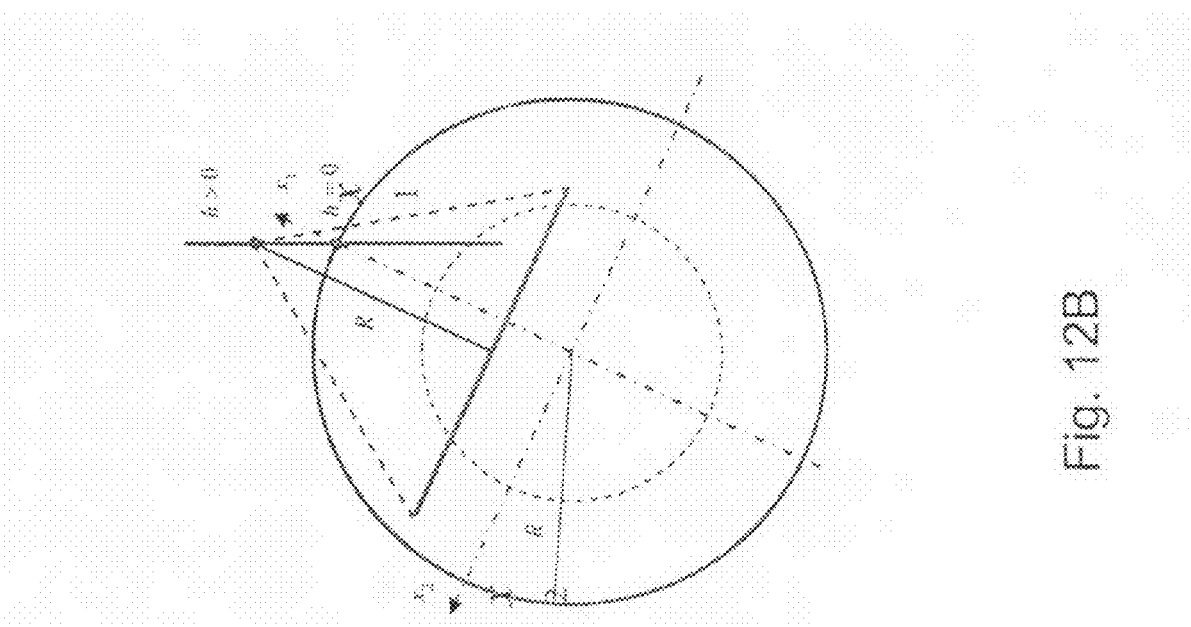
FIG. 12B is another view of coordinates according to an embodiment of the present invention.
Figure 12A:
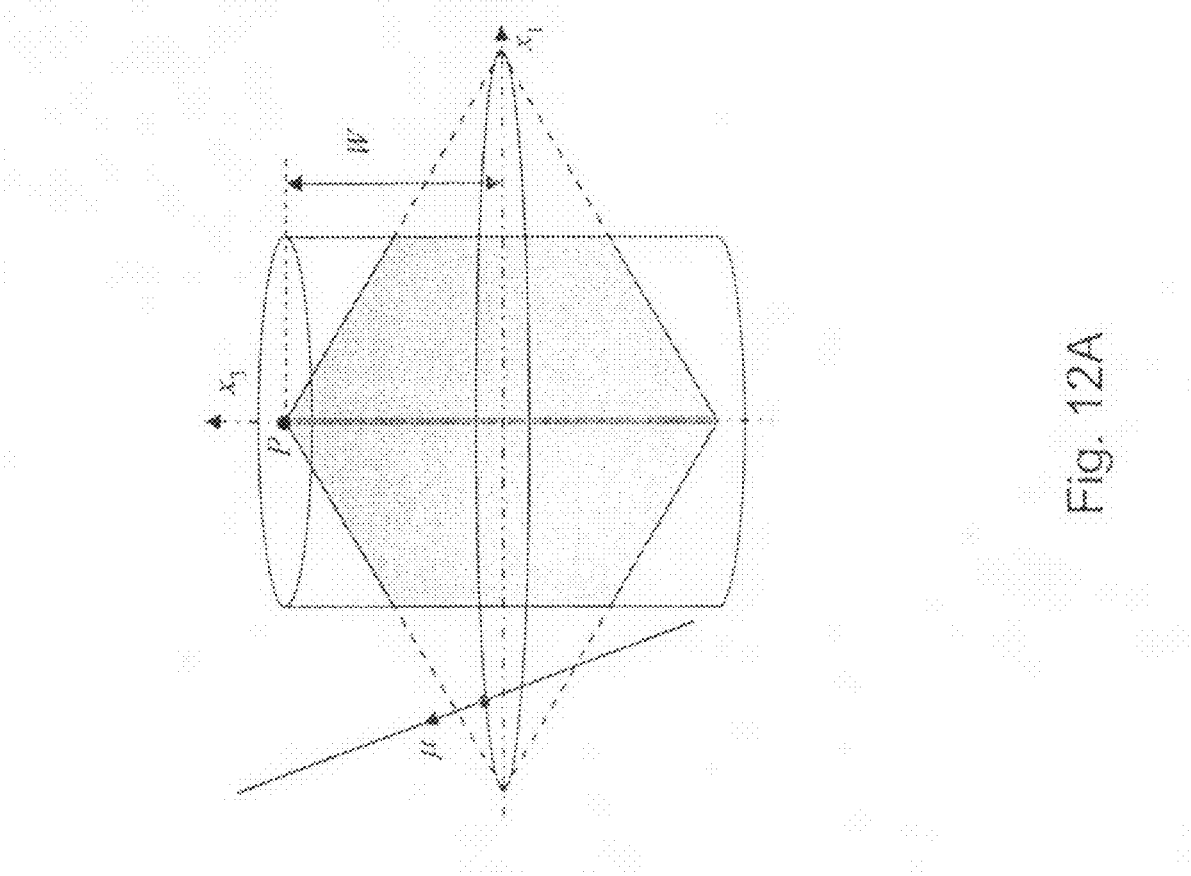
FIG. 12A is an isometric view of coordinates according to an embodiment of the present invention.

According to this embodiment, let ξ be the gantry tilt angle as shown in FIG. 11A, and $\bar{\mu}$ the unit directional vector of the line trajectory μ as shown in FIG. 12A, where the shaded region of FIG. 12A represents the reconstruction volume (i.e., the largest region where no data extrapolation is required). It is convenient to rotate axes $x_1$, $x_2$ such that the point of intersection between the circle and line, $\bar{y}_0$, has coordinates (R, 0, 0), as shown in FIG. 12B.

In this embodiment, vector $\bar{\mu}$ has coordinates $$\bar{\mu}(\mu_1, \mu_2, \mu_3) = (\sin \lambda_1 \sin \xi, \cos \lambda_1 \sin \xi, \cos \xi) \quad (16)$$

and the coordinates of the line source are given by:

$$\bar{y}(h) = \bar{y}_0 + \bar{\mu}h = (R + h\mu_1, h\mu_2, h\mu_3). \quad (17)$$

Equation (18) is for filtering lines on the flat detector, and equation (19) is for filtering lines on the curved detector, as follows:

$$v_L(u; h, \rho_L) = \frac{h\mu_3(2\rho_L u + R(\rho_L^2 - 1))}{2R - h(\mu_1(\rho_L^2 - 1) - 2\mu_2\rho_L)} \quad (18)$$

$$w_L(\gamma; h, \rho_L) = \frac{R h \mu_3 (2\rho_L \sin\gamma + (\rho_L^2 - 1)\cos\gamma)}{2R - h(\mu_1(\rho_L^2 - 1) - 2\mu_2\rho_L)} \quad (19)$$

In equations (18) and (19), $\rho_L$ is a filtering parameter based on the equation $$\rho_L = -\cot\left(\frac{\lambda}{2}\right),$$

where λ is the angle to the point of tangency of the filtering plane.

The range of the line scan is determined by $$h_{max} = \frac{2WR(R\mu_3 + W\mu_1)}{R^2\mu_3^2 - W^2(\mu_1^2 + \mu_2^2)}, \, h > 0. \quad (20)$$

It can be easily seen that in the case of zero gantry tilt, equation (20) reduces to $h_{max}$=2W, as described above.

All embodiments of the present invention conveniently may be implemented using a conventional general purpose computer or micro-processor programmed according to the teachings of the present invention, as will be apparent to those skilled in the computer art. Appropriate software may readily be prepared by programmers of ordinary skill based on the teachings of the present disclosure, as will be apparent to those skilled in the software art. In particular, the computer housing may house a motherboard that contains a CPU, memory (e.g., DRAM, ROM, EPROM, EEPROM, SRAM, SDRAM, and Flash RAM), and other optional special purpose logic devices (e.g., ASICS) or configurable logic devices (e.g., GAL and reprogrammable FPGA). The computer also includes plural input devices, (e.g., keyboard and mouse), and a display card for controlling a monitor. Additionally, the computer may include a floppy disk drive; other removable media devices (e.g. compact disc, tape, and removable magneto-optical media); and a hard disk or other fixed high density media drives, connected using an appropriate device bus (e.g., a SCSI bus, an Enhanced IDE bus, or an Ultra DMA bus). The computer may also include a compact disc reader, a compact disc reader/writer unit, or a compact disc jukebox, which may be connected to the same device bus or to another device bus.

Examples of computer readable media associated with the present invention include compact discs, hard disks, floppy disks, tape, magneto-optical disks, PROMs (e.g., EPROM, EEPROM, Flash EPROM), DRAM, SRAM, SDRAM, etc. Stored on any one or on a combination of these computer readable media, the present invention includes software for controlling both the hardware of the computer and for enabling the computer to interact with a human user. Such software may include, but is not limited to, device drivers, operating systems and user applications, such as development tools. Computer program products of the present invention include any computer readable medium which stores computer program instructions (e.g., computer code devices) which when executed by a computer causes the computer to perform the method of the present invention. The computer code devices of the present invention may be any interpretable or executable code mechanism, including but not limited to, scripts, interpreters, dynamic link libraries, Java classes, and complete executable programs. Moreover, parts of the processing of the present invention may be distributed (e.g., between (1) multiple CPUs or (2) at least one CPU and at least one configurable logic device) for better performance, reliability, and/or cost. For example, an outline or image may be selected on a first computer and sent to a second computer for remote diagnosis.

The invention may also be implemented by the preparation of application specific integrated circuits or by interconnecting an appropriate network of conventional component circuits, as will be readily apparent to those skilled in the art.

The source of image data to the present invention may be any appropriate image acquisition device such as an X-ray machine or CT apparatus. Further, the acquired data may be digitized if not already in digital form. Alternatively, the source of image data being obtained and process ed may be a memory storing data produced by an image acquisition device, and the memory may be local or remote, in which case a data communication network, such as PACS (Picture Archiving Computer System), may be used to access the image data for processing according to the present invention.

Performance of an embodiment of the invention, including complete elimination of the cone beam artifact, was evaluated using an example of simulated noise-free torso dated with a spine that has rapid transitions in the z-direction.

Figure 13A:
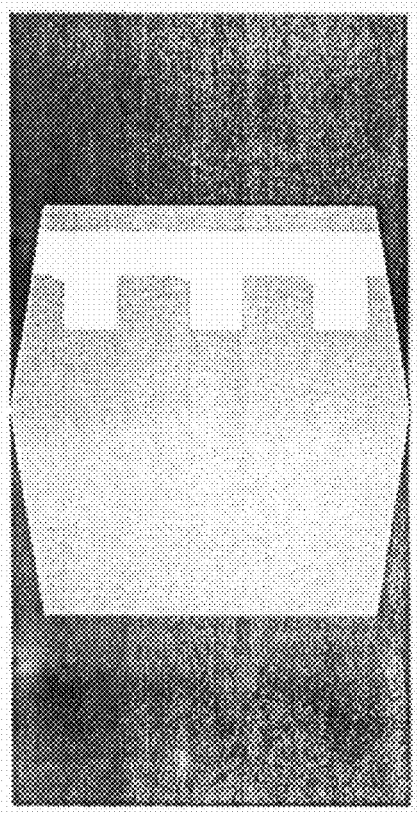
FIG. 13A is an example of a reconstructed image of simulated data using a conventional circular FDK method.

FIG. 13A is an example of a reconstructed image of the simulated data using a conventional circular FDK method.

Figure 13B:
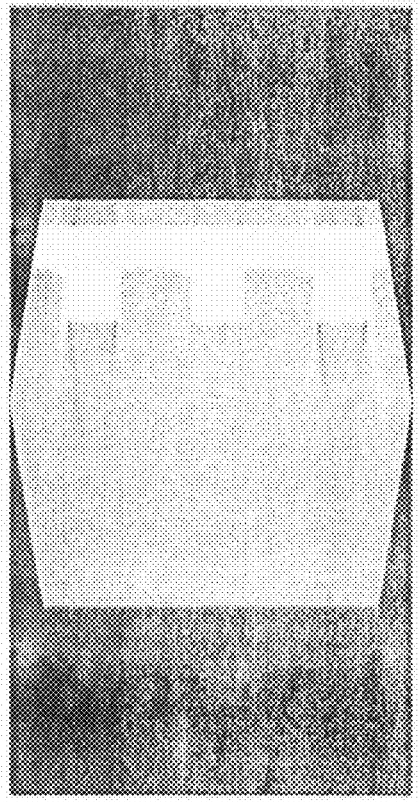
FIG. 13B is an example of a reconstructed image of the simulated data using an embodiment of the invention having ramp based circle data reconstruction combined with line data reconstruction.

FIG. 13B is an example of a reconstructed image of the simulated data using an embodiment of the invention having ramp based circle data reconstruction combined with line data reconstruction, as described above. The display window in FIGS. 13A and 13B is L/W=0/200.

Performance of an embodiment of the invention was also evaluated using a dynamic torso phantom, which realistically simulates human heart motion.

FIGS. 14A-14F are examples of the results of the simulated heart motion evaluation.

Figures 14A, 14B, 14C, 14D, 14E, 14F:
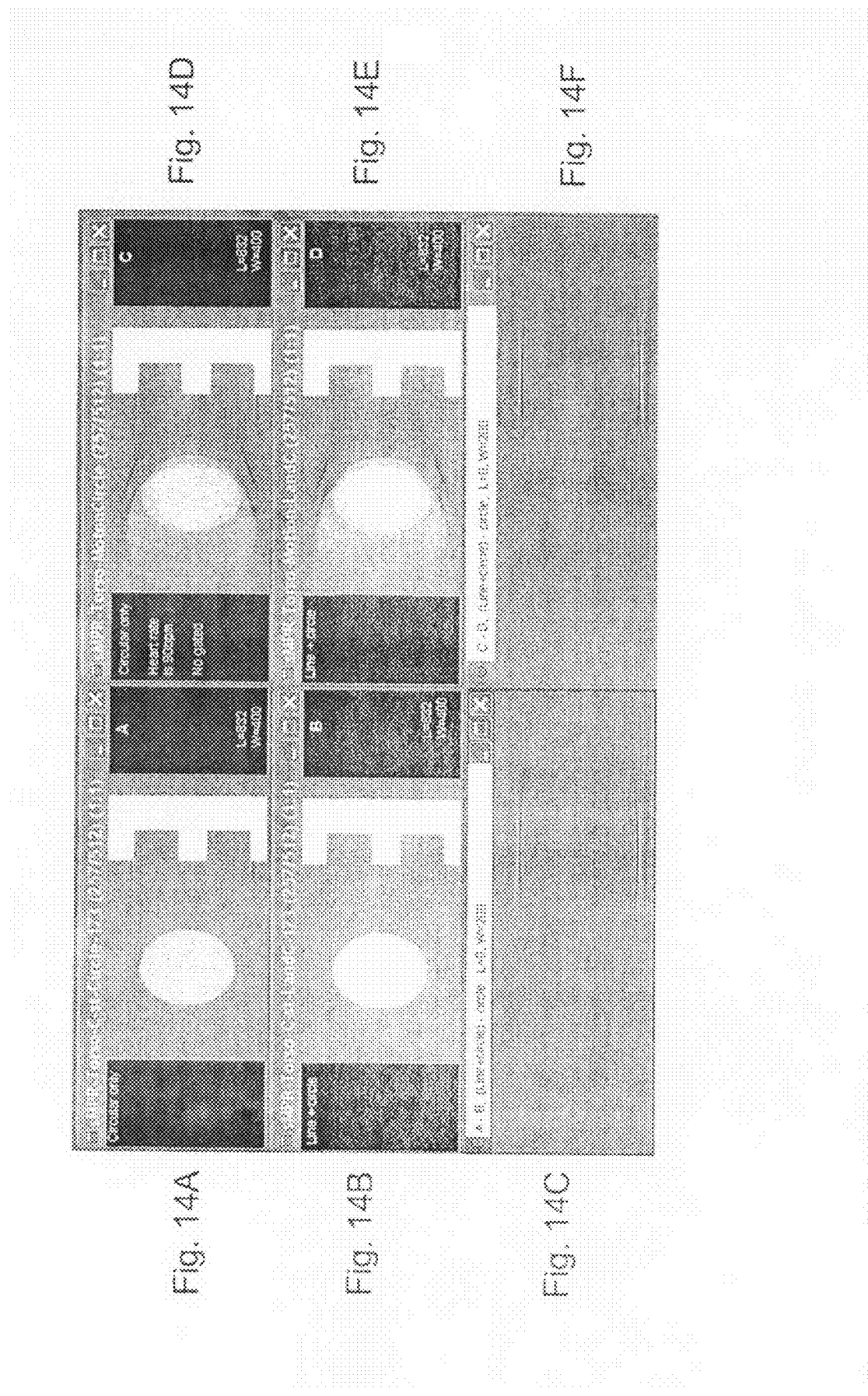
FIG. 14A is a reconstructed image showing the effects of heart motion when the image is reconstructed using only gated circle scan data.
FIG. 14B is a reconstructed image showing the effects of heart motion when the image is reconstructed using gated circle scan data and non-gated line data according to an embodiment of the present invention.
FIG. 14C is an image of the difference between FIGS. 14A and 14B.
FIG. 14D is a reconstructed image showing the effects, of heart motion when the image is reconstructed using only non-gated circle scan data.
FIG. 14E is a reconstructed image showing the effects of heart motion when the image is reconstructed using non-gated circle scan data and non-gated line data.
FIG. 14F shows the difference between FIGS. 14D and 14E.

FIG. 14A is a reconstructed image showing the effects of heart motion when the image is reconstructed using only gated circle scan data.

FIG. 14B is a reconstructed image showing the effects of heart motion when the image is reconstructed using gated circle scan data and non-gated line data according to an embodiment of the present invention.

FIG. 14C shows the difference between FIGS. 14A and 14B.

FIG. 14D is a reconstructed image showing the effects of heart motion when the image is reconstructed using only non-gated circle scan data.

FIG. 14E is a reconstructed image showing the effects of heart motion when the image is reconstructed using non-gated circle scan data and non-gated line data.

FIG. 14F shows the difference between FIGS. 14D and 14E.

The example images show that reconstruction is improved and cone beam artifacts are removed by gating the circle scan data without requiring gating of the line scan data. Further, reduction of the cone beam artifacts is not affected by organ motion in the circle scan data.

The gated circle data has the effect of limiting the circle data only to include images captured during a same particular phase of heart activity when the heart is relatively non-moving. Gating may be performed by only creating scan data during the desired heart phase (e.g., only radiating the patient with the source at times corresponding to that phase), or by capturing data during plural heart cycles and only extracting data corresponding to a desired heart cycle time.

Figure 15:
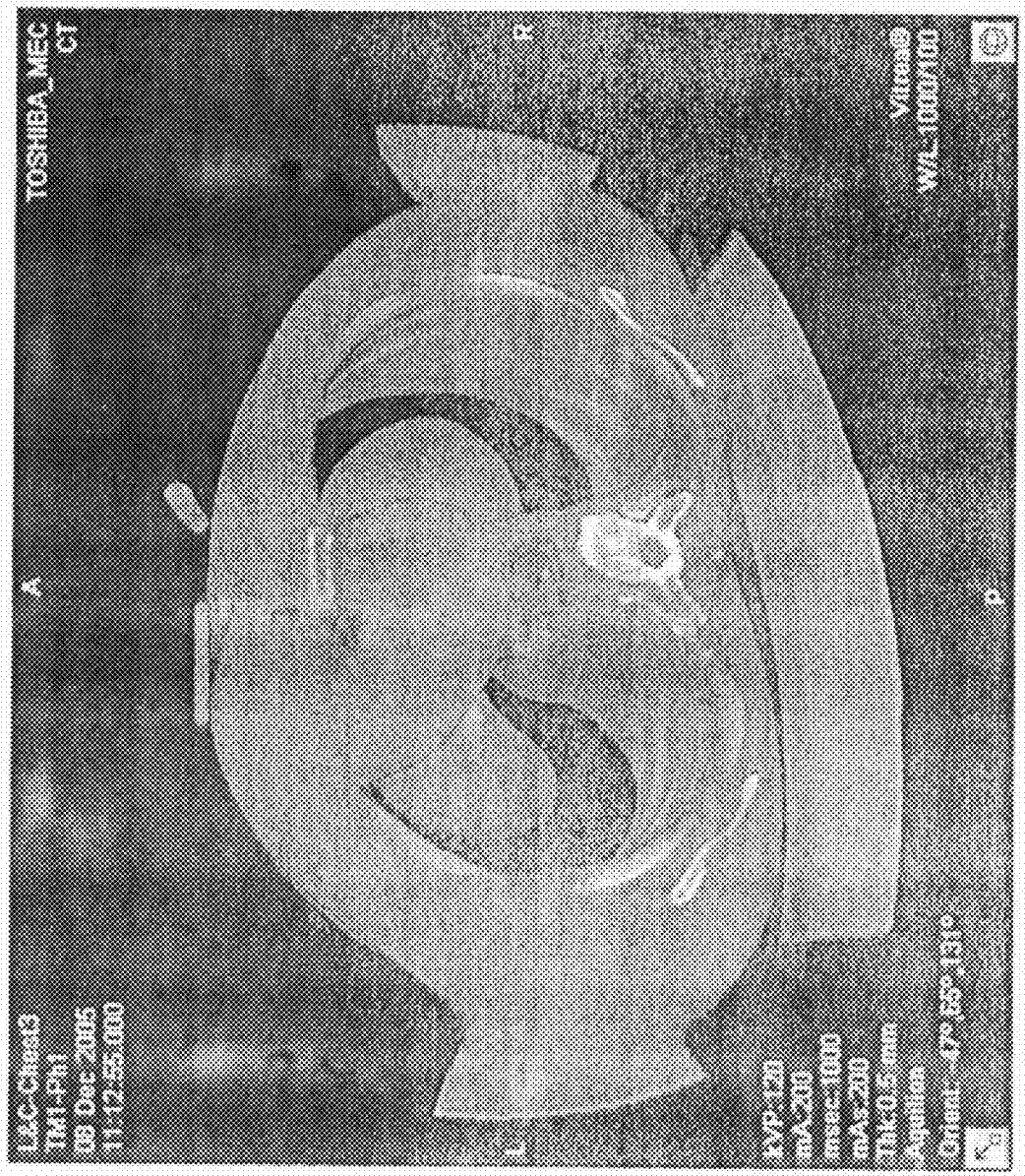
FIG. 15 is an image of an anthropomorphic phantom.

Projection data of an anthropomorphic phantom were acquired on the 256-slice scanner along the circle and line trajectory. FIG. 15 is an image of the anthropomorphic phantom. Several datasets were acquired to investigate performance depending on the line radiation dose tube current (mA) settings and body part, i.e., head, chest, and abdomen. Scanning parameters for this example are given in Table 1. In this example, the full cone angle is over 12 degrees. Note that the tube current for the line scan is much lower than that of the circle scan.

Figure 16B:
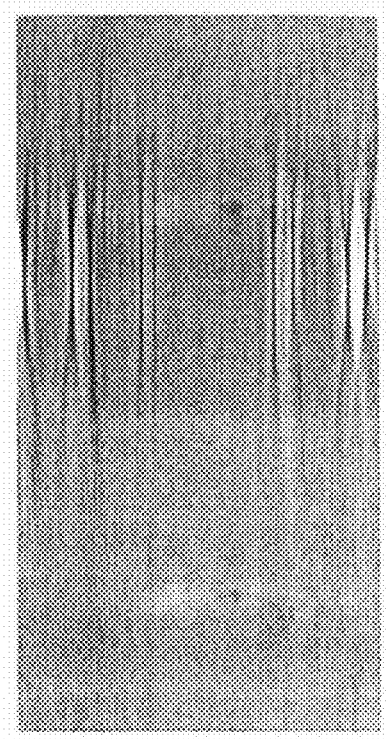
FIG. 16B is an example of line reconstruction data.
Figure 16A:
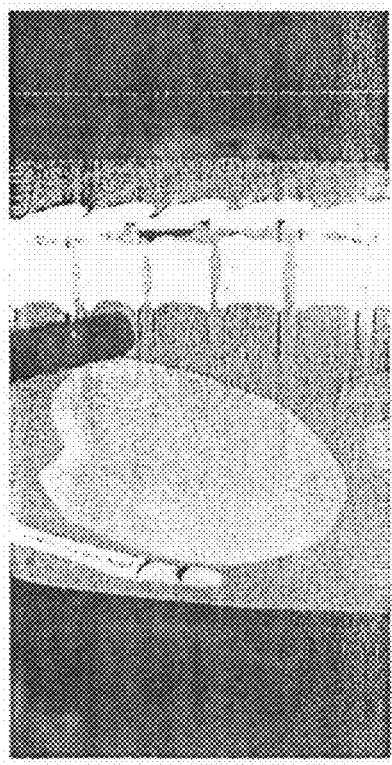
FIG. 16A is an example of a reconstructed image using only FDK circle scan data.
Figure 16C:
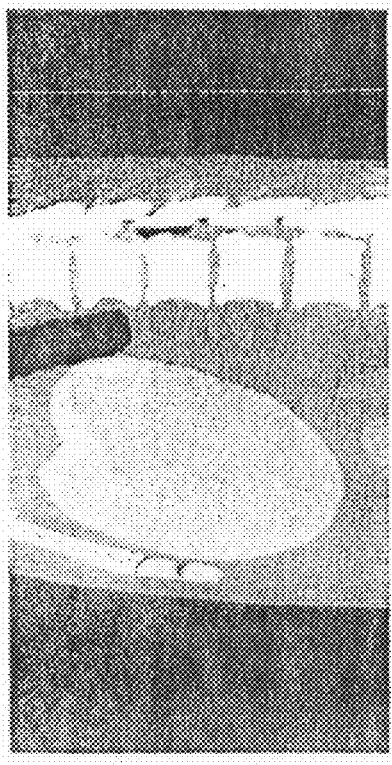
FIG. 16C is an example of a reconstructed image using an embodiment of the present invention.

FIG. 16A is an example of a reconstructed image using only FDK circle scan data. FIG. 16B is an example of line reconstruction data. FIG. 16C is an example of a reconstructed image using an embodiment of the present invention, as described above. In the examples of FIGS. 16A-16C, the display window is L/W=40/200. This example further illustrates that the inventive approach eliminates the visible cone beam artifact.

Further, FIG. 16B illustrates that the line scan data contributes only to the cone beam artifact correction and does not include any anatomical structure. The line scan data represents high-frequencies only in the z-direction, and only very low frequencies in the x-y planes.

Further, it is possible to perform the line scan using a very low dose of radiation, corresponding to a very low tube current (mA). Performance evaluations of embodiments of the present invention as described above show that cone beam artifacts may be reduced using a tube current of less than 50 mA, or preferably less than 20 mA, or about 10 mA.

Figure 17A:
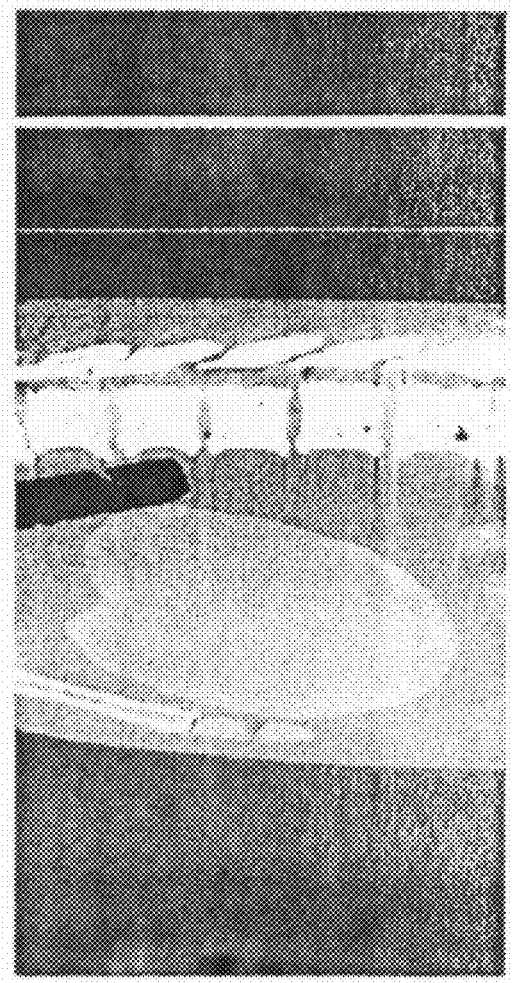
FIG. 17A is an example of an image reconstructed using only FDK circle data.
Figure 17B:
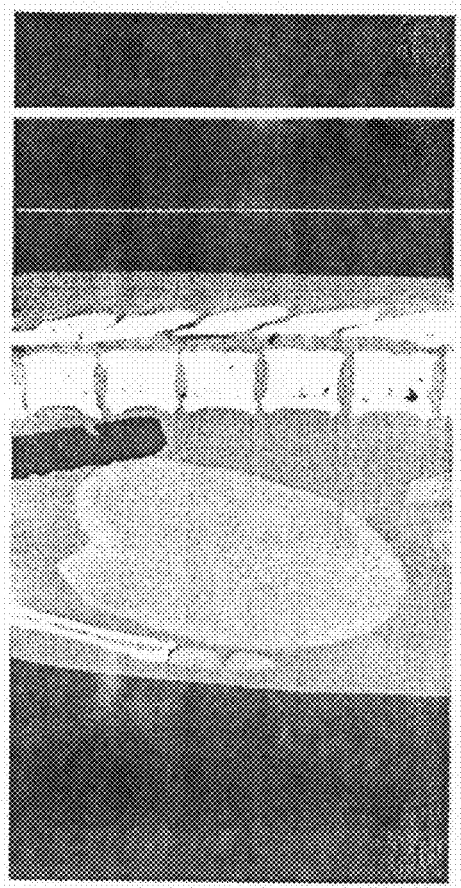
FIG. 17B is an example of an image reconstructed using circle and line data according to an embodiment of the present invention, with a tube current of 50 mA.
Figure 17C:
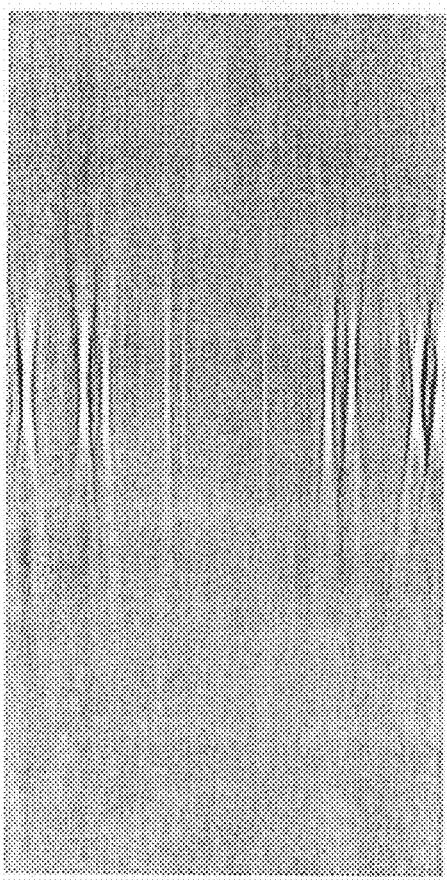
FIG. 17C is an example of only the line data used in the example of FIG. 17B.
Figure 17D:
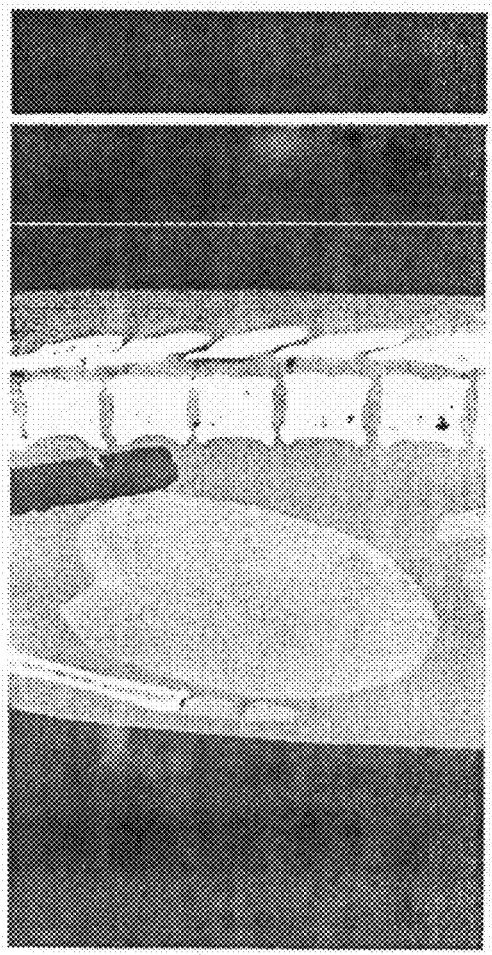
FIG. 17D is an example of an image reconstructed using circle and line data according to an embodiment of the present invention, with a tube current of 30 mA.
Figure 17E:
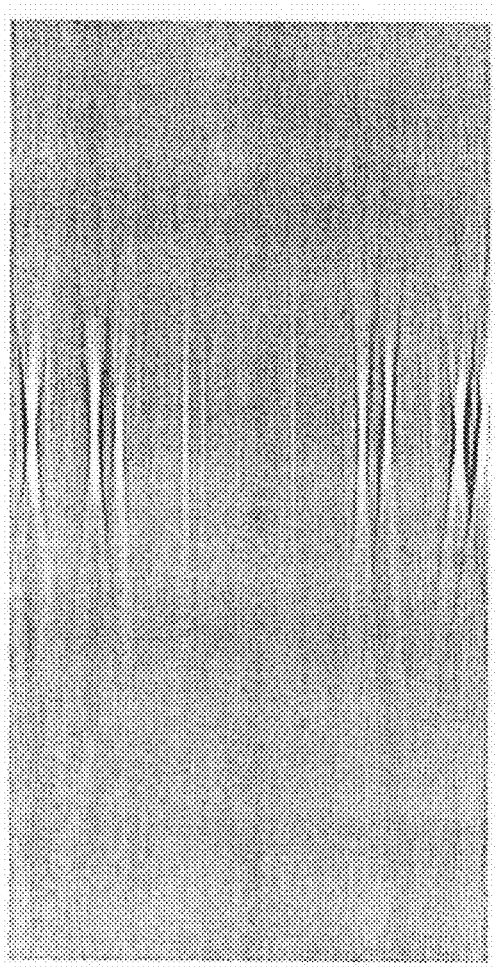
FIG. 17E is an example of only the line data used in the example of FIG. 17D.
Figure 17F:
FIG. 17F is an example of an image reconstructed using circle and line data according to an embodiment of the present invention, with a tube current of 50 mA.
Figure 17G:
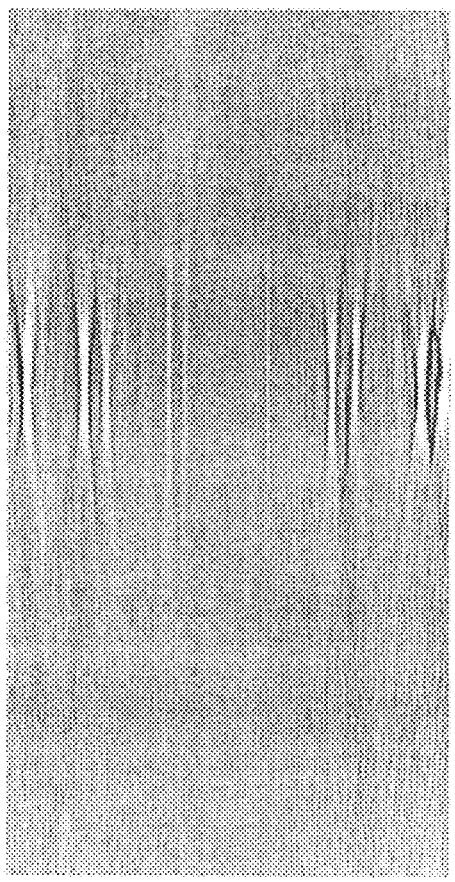
FIG. 17G is an example of only the line data used in the example of FIG. 17F.

FIG. 17A is an example of an image reconstructed using only FDK circle data. FIG. 17B is an example of an image reconstructed using circle and line data according to an embodiment of the present invention, with a tube current of 50 mA. FIG. 17C is an example of only the line data used in the example of FIG. 17B. FIG. 17D is an example of an image reconstructed using circle and line data according to an embodiment of the present invention, with a tube current of 30 mA. FIG. 17E is an example of only the line data used in the example of FIG. 17D. FIG. 17F is an example of an image reconstructed using circle and line data according to an embodiment of the present invention, with a tube current of 50 mA. FIG. 17G is an example of only the line data used in the example of FIG. 17F. Accordingly, this example shows that the additional dose of the line scan to the patient is minimal, while still reducing the cone beam artifact.

Figure 18A:
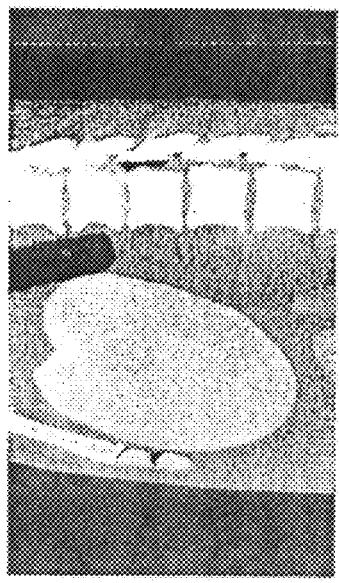
FIG. 18A is an image reconstructed using only FDK circle data reconstruction.
Figure 18B:
FIG. 18B is an image reconstructed according to an embodiment of the invention with accurate couch position information.
Figure 18C:
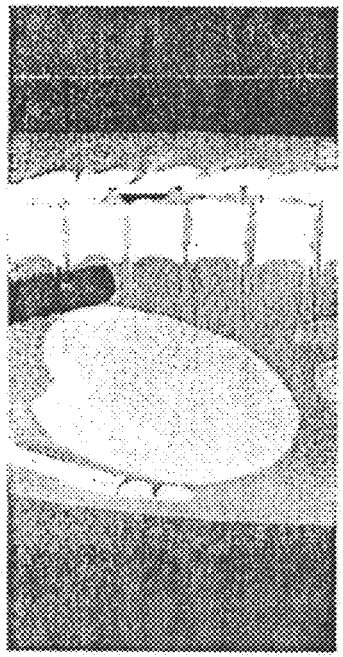
FIG. 18C is an image reconstructed with inaccurate couch position information.

Further, the embodiments described above may be sensitive to inaccuracies in the data regarding the couch position. For example, FIG. 18A is an image reconstructed using only FDK circle data reconstruction. FIG. 18B is an image reconstructed according to an embodiment of the invention described above, and with accurate couch position information. FIG. 18C is an image reconstructed according to an embodiment of the invention described above, and with inaccurate couch position information, and in particular, +/−0.3 mm inaccuracy in the couch position information. The example of FIG. 18C shows streak artifacts resulting from the inaccurate couch position information.

A further embodiment of the present invention includes compensating for a couch inaccuracy by adjusting a reconstruction parameter that is used to produce either one or both of the line reconstruction or circle reconstruction. The reconstruction parameter is determined based on a correlation between the circle projection data and circle projection data near the common point of the circular and linear trajectories (note that at this point projections from both trajectories should coincide).

Figure 19B:
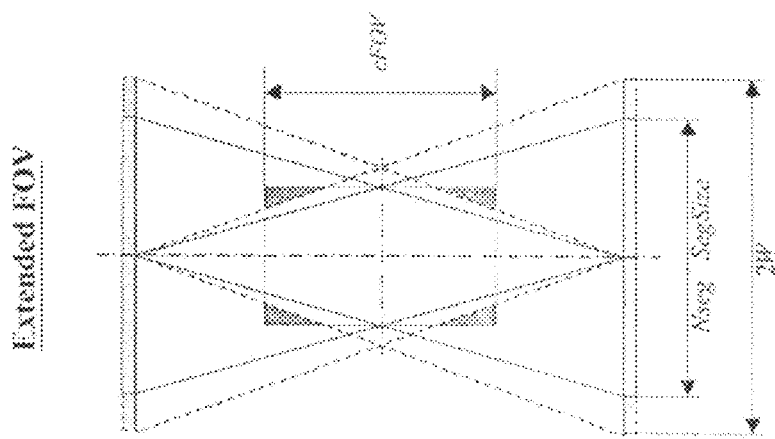
FIG. 19B is a view of an extended FOV obtained using the virtual expanded detector.
Figure 19A:
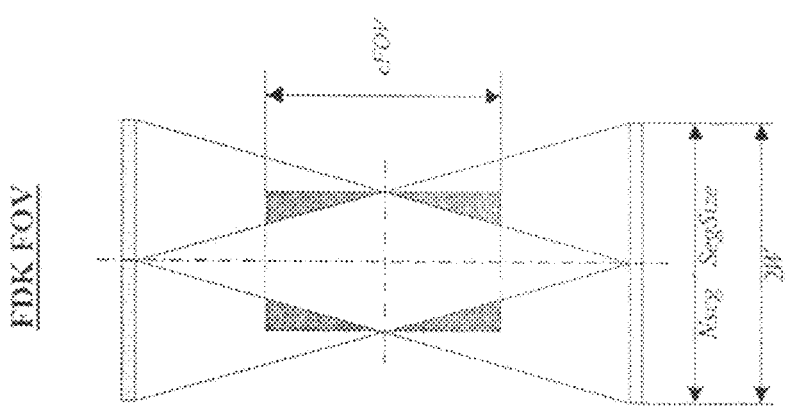
FIG. 19A is a view of a FOV obtained with FDK circle scan only.

The reconstruction volume coverage of the line scan may be further reduced by using a virtual expanded detector. In FDK circle path only reconstruction, the FOV, as shown in the example of FIG. 19A, is limited by a hexagonal shape (e.g., hexagon shaped ROI region in FIG. 19A. To increase the FDK FOV, the virtual expanded detector may be used. Unmeasured data in the extended detector rows may be obtained by duplicating measured data in the boundary detector rows, or by extrapolation. FIG. 19B shows extended FOV obtained using the virtual expanded detector. Note that reconstruction in the extended region outside the FDK FOV is less accurate than inside the FDK FOV.

FIGS. 20A-20F are plural line view in a method of reducing an exposure dose of the line scan using line scan collimation. In each view, h is the view z-coordinate on the line scan path, and the shaded region shows data used in the line scan backprojection step. Further, although FIGS. 20B-20F only show the case when h>0 (upper portion of the line scan), the case when h<0 is symmetric and may be handled in a corresponding fashion. Thus, according to this embodiment, the dose of radiation received by the patient during the line scan may be reduced using active collimation to prevent radiation outside the shaded region.

Figure 21:
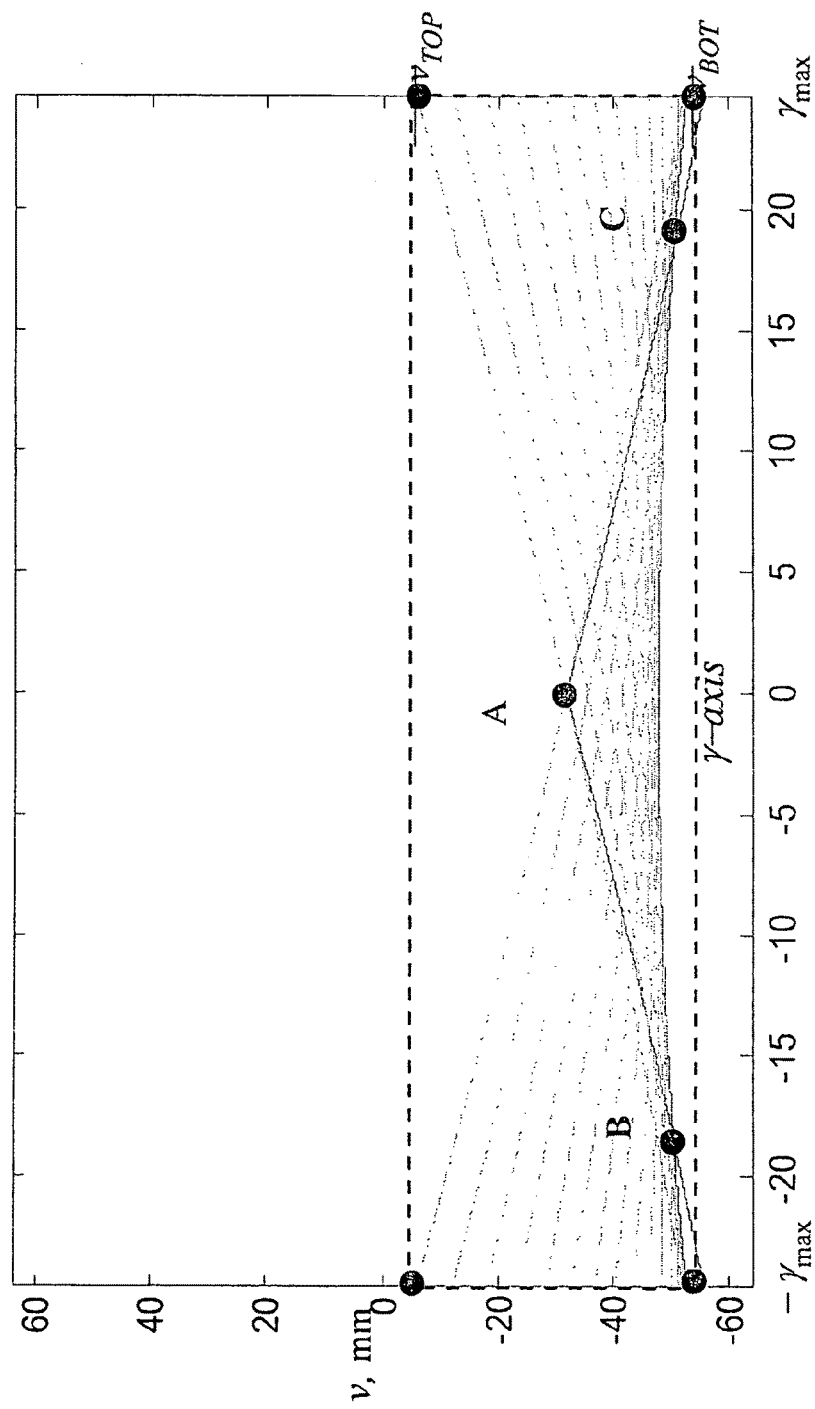
FIG. 21 is an example of a collimation window for active collimation.

FIG. 21 is an example of a collimation window for active collimation. According to this example, using equations (9), (10), (13), (15) we obtain for vertical top and bottom boundaries, $v_{TOP}(h)$ and $v_{BOT}(h)$, respectively:

$$v_{TOP}(h) = -h\left(\frac{1-\rho_X}{2}\cos\gamma_{max} - \sqrt{\rho_X}\sin\gamma_{max}\right) \quad (21)$$

$$v_{BOT}(h) = -\frac{h}{2\cos\gamma_{max}} \quad (22)$$

In addition, equation (21) is only used to calculate $v_{TOP}$ for h>5.81 mm; for h<5.81 mm, $v_{TOP}$=W.

Figure 22:
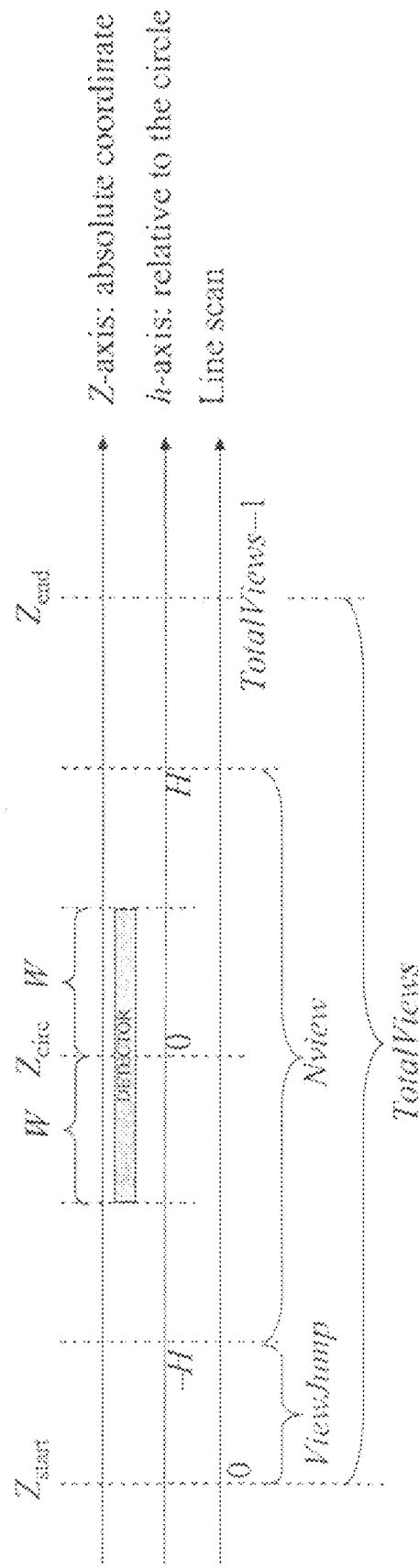
FIG. 22 is a further illustration of geometry according to the present invention.

FIG. 22 is a further illustration of geometry according to the present invention. According to the present invention, the following parameters are determined by the system operator according to the scan conditions:

Detector half-size $W=Nseg*Wseg/2$ (23)

Zstart Line scan start z-position
Zend Line scan end z-position
Zcirc Circle z-position
Total Views Total number of line views The following parameters are calculated according to embodiments of the present invention:

Half-line-scan length for recon H=2W (24)

Nview Number of views for reconstruction
ViewJump First view for reconstruction.
Δh Line view pitch
h Line view position, relative to the circle
Further, according to:

$$\Delta h = \frac{Z_{end} - Z_{start}}{TotalViews - 1} \quad (25)$$

or, $$\Delta h = \frac{Z_{end} - Z_{start}}{TotalViews} \quad (26)$$

equation (27) is satisfied.

$h(\text{view})=Z\text{start}-Z\text{circ}+\text{view}\cdot\Delta h$ (27).

and, such definition is independent if Zend>Zstart, or Zend<Zstart.). Further, $N\text{view}=2W/\Delta h$ (28)

ViewJump=(Zcirc−Zstart−H)/Δh (29)

Figure 23A:
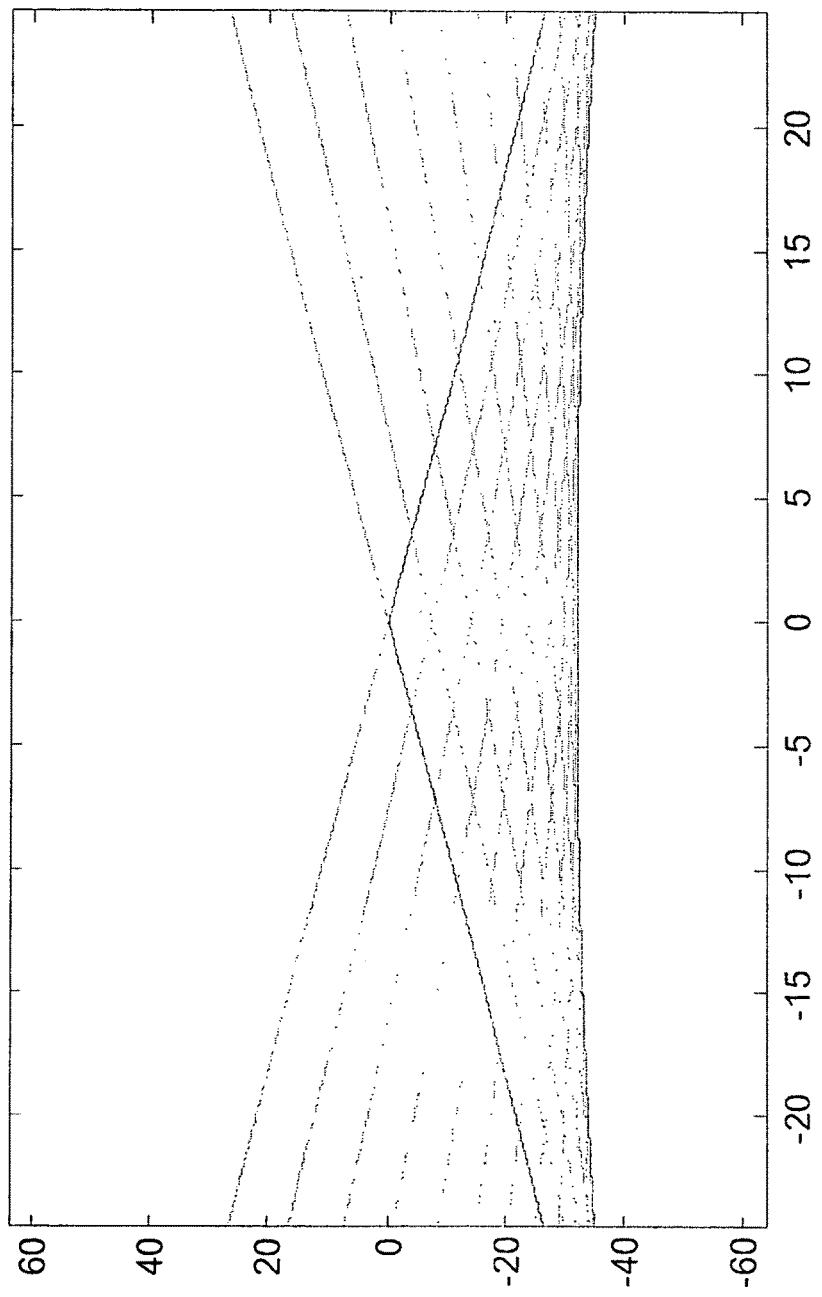
FIG. 23A is a graph of filter lines in line scan data.

FIG. 23A is a graph of filter lines in line scan data.

Figure 23B:
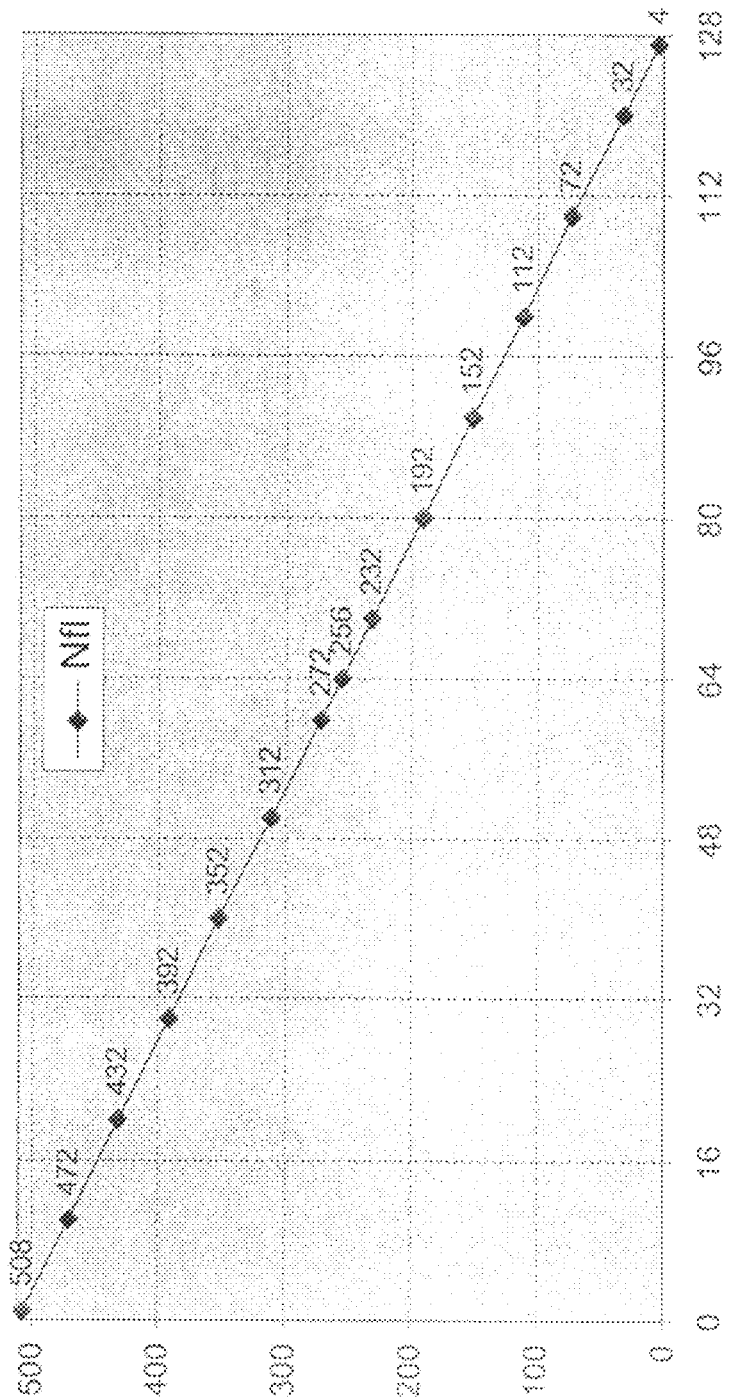
FIG. 23B is a graph of a number of the filter lines in line scan data.

FIG. 23B is a graph of a number of the filter lines in line scan data. In particular, according to this example, the number of filtering lines is proportional to the length of line segment AC=W−h/2. Preferably, the number of filtering lines Nfl is calculated as follows:

Nfl=(W−|h|/2)/SegSize*4. (30)

FIG. 23B is a graph of a number of filter lines Nfl.

Figure 24:
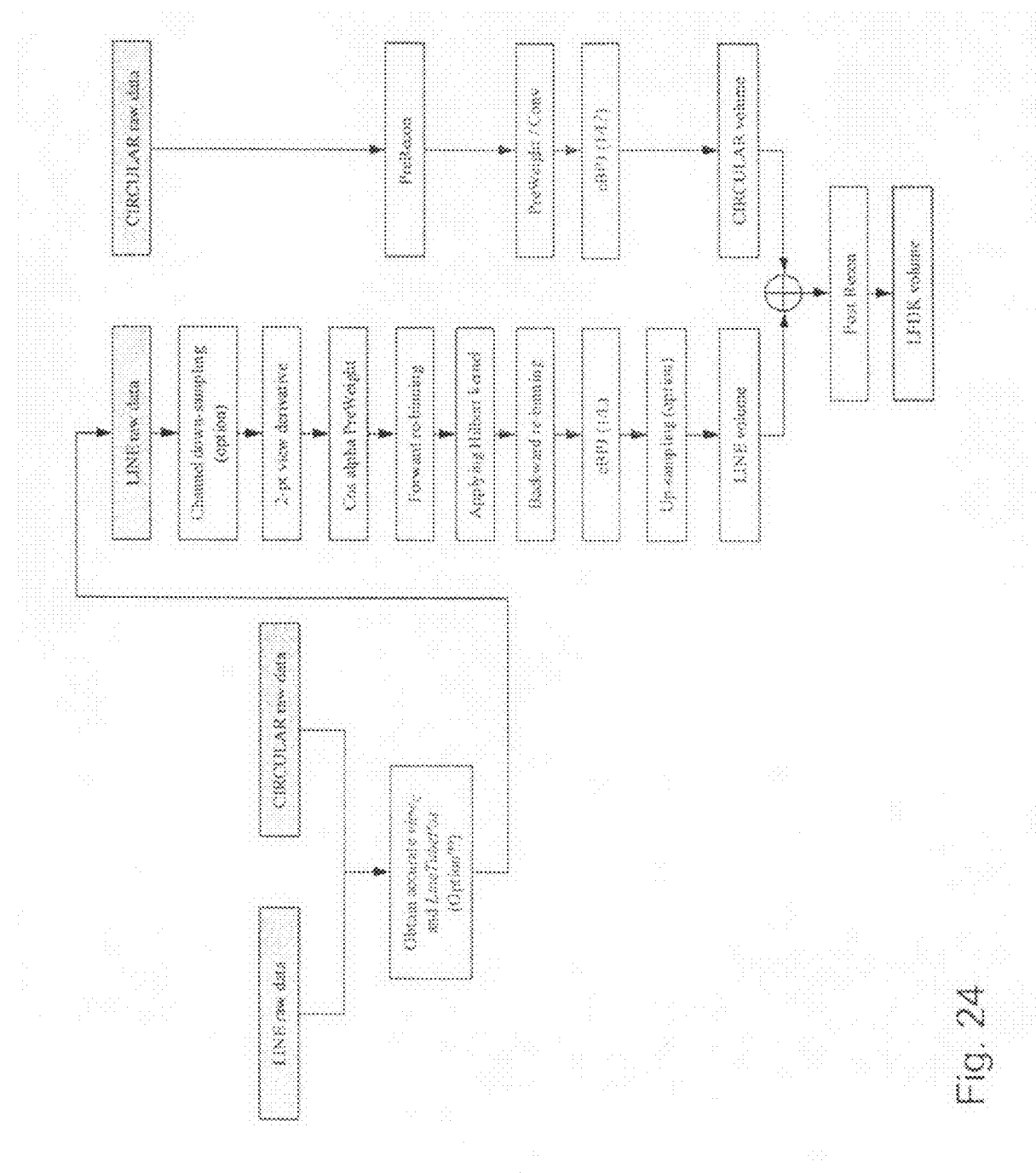
FIG. 24 is block diagram of a method of a line and circle algorithm according to another embodiment of the present invention.

FIG. 24 is block diagram of a method of a line and circle algorithm according to another embodiment of the present invention, in which a number of samples (channels) in the collected line data can be reduced by a factor $K_{DS}$, where the down-sampling factor $K_{DS}$ can be equal to 2, 3, 4, or 5, for example.

Figure 25C:
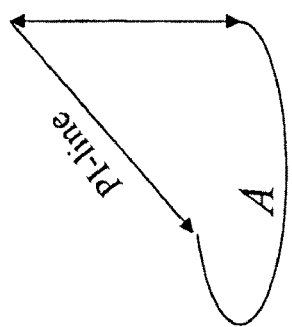
FIG. 25C is another representation of the family of curves in FIG. 25A.
Figure 25D:
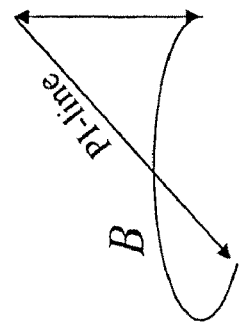
FIG. 25D is another representation of the family of curves in FIG. 25B.
Figure 25A:
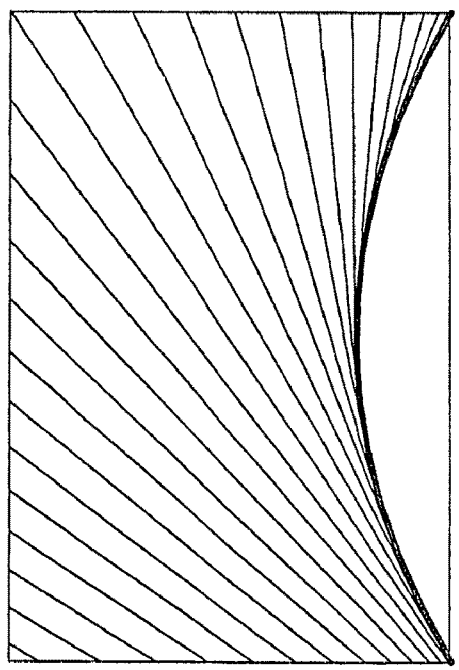
FIG. 25A is an example of a family of cures used in a short scan convolution.
Figure 25B:
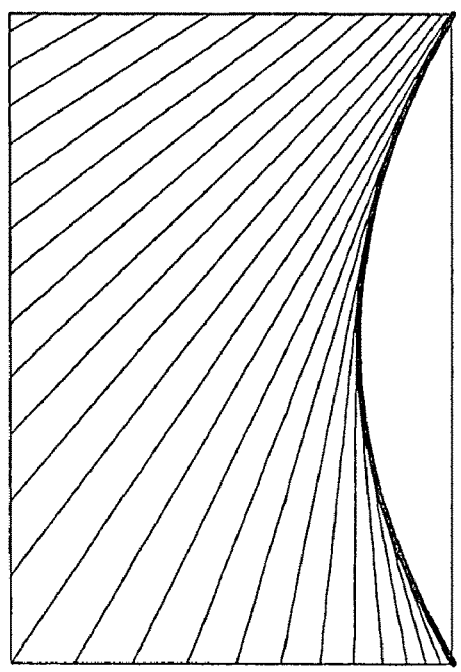
FIG. 25B is an example of another family of curves used in a short scan convolution.

FIGS. 25A and 25B show an example of two families of curves used in short scan convolutions. FIG. 25C and 25D show a further representation of the two families of curves. Note that filtering planes (or curves) are obtained by intersection of the filtering planes with the detector plane (flat or cylindrical, depending on the detector type). In particular, the curves shown in FIG. 25A correspond to the filtering planes tangential to the arc A in FIG. 25C, and the curves in FIG. 25B correspond to the filtering planes tangential to arc B in FIG. 25D.

According to an embodiment of the invention, a short scan, which scans along only a portion of a circle arc, uses only one family of lines (i.e., one of FIG. 25A or FIG. 25B) depending on which part of the circle scan is used. Each family covers the detector only one time. That is, for each detector pixel there is only one filtering line.

Figure 26A:
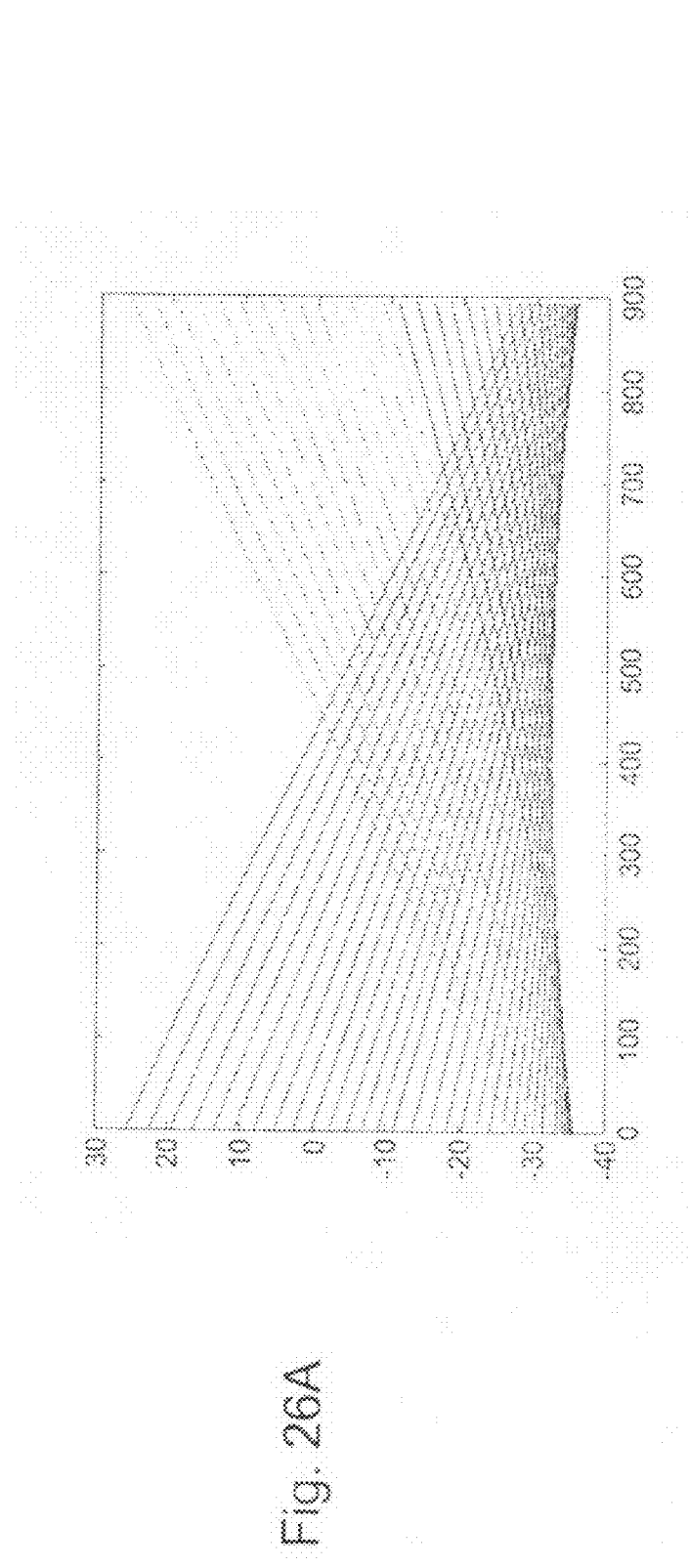
FIG. 26A is an example of a full scan convolution in which lines from plural families.

FIG. 26A is an example of a full scan convolution in which lines from plural families (i.e., all the lines in FIG. 26A) are used. This family covers the detector two times. That is, for each detector pixel there are two filtering lines. To obtain values corresponding to each filtering line, take the difference between the two values:

ConvData=ConvDataA−ConvDataB (31)

Figure 26B:
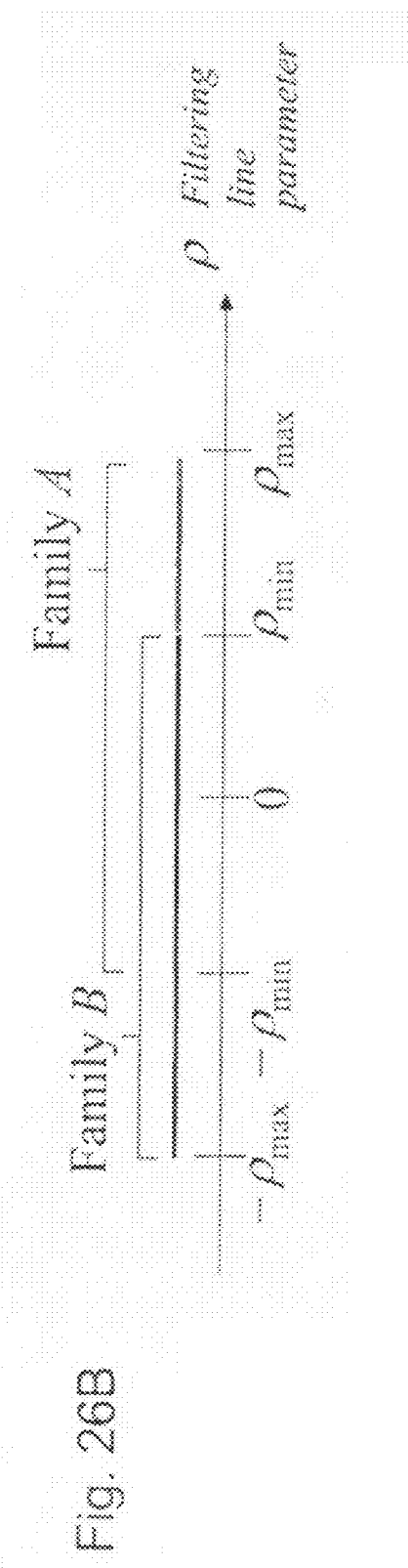
FIG. 26B is a single dimensional view of the overlap of the lines of the two families of FIG. 26A.

FIG. 26B is a single dimensional view of the overlap of the lines of the two families of FIG. 26A.

Figure 27A:
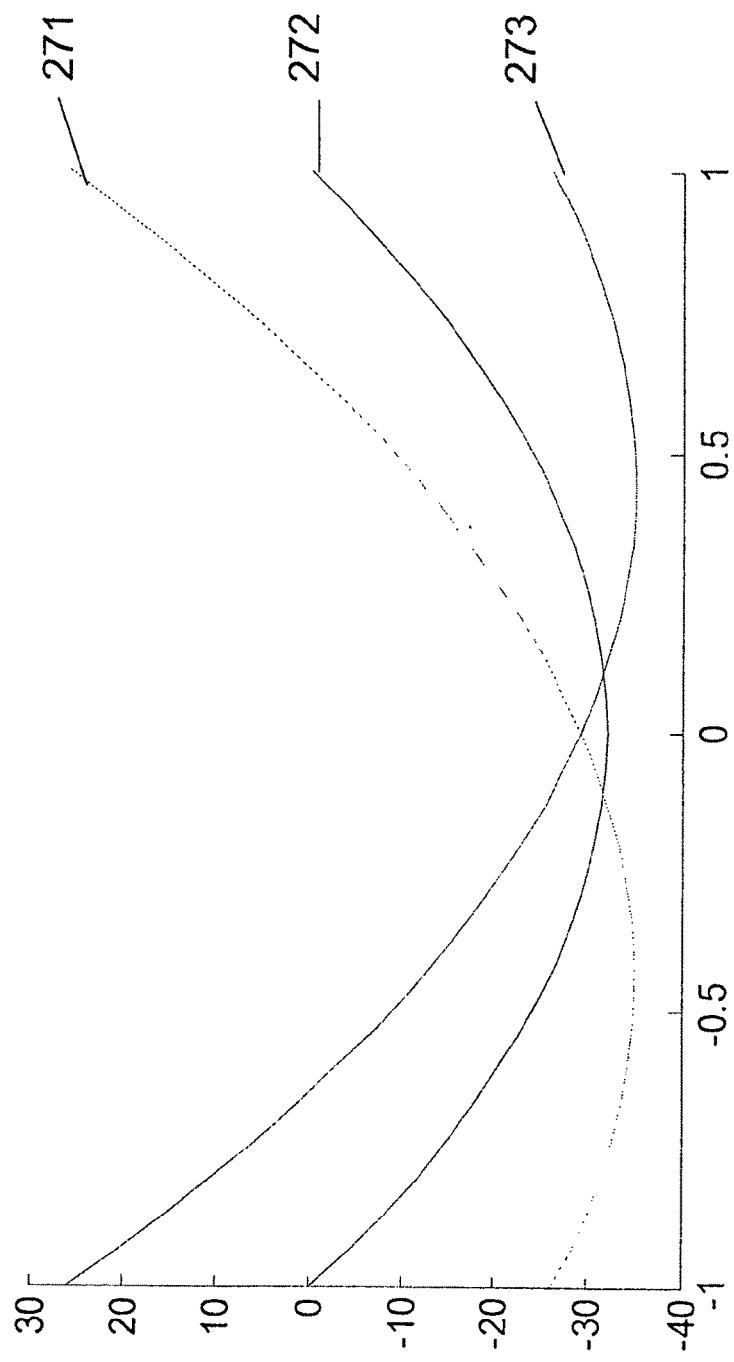
FIG. 27A is an example of inverse rebinning curves according to an embodiment of the present invention.
Figure 27B:
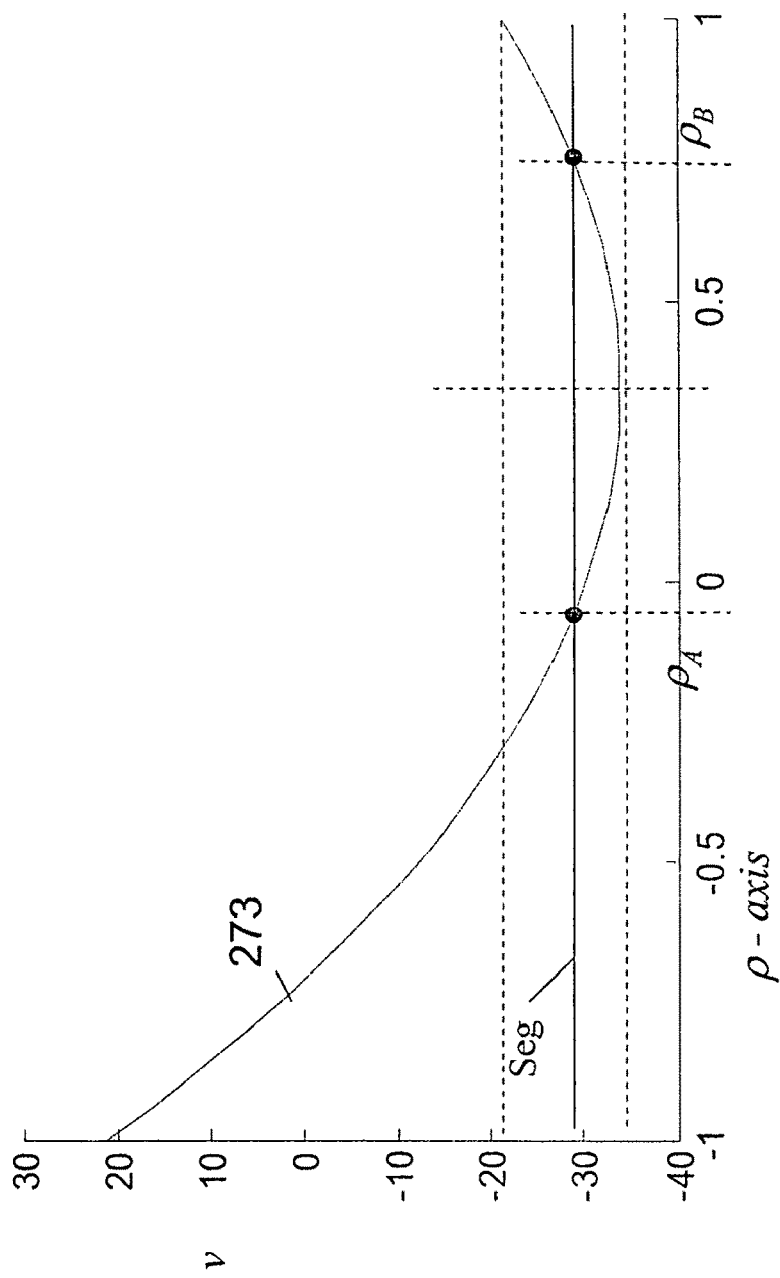
FIG. 27B is an example of reverse rebinning processing.

FIGS. 27A and 27B are examples of reverse rebinning according to an embodiment of the present invention. FIG. 27A shows inverse rebinning curve 270 for channel 10, inverse rebinning curve 271 for channel 447 (e.g., a center channel), and inverse rebinning curve 272 for channel 887.

FIG. 27B is an example of reverse rebinning processing. According to this example, first obtain $\rho_A$ and $\rho_B$ of the intersection of the segment coordinate Seg with the inverse rebinning curve 274. Next, interpolate CONV values at these $\rho_A$ and $\rho_B$ and take the difference:

$$\text{ConvFinal}(ch, seg) = \text{ConvRebin}(ch, rA) - \text{ConvRebin}(ch, rB) \tag{32}$$

FIG. 28A is an example of expanding a reconstructed volume of interest (VOI) according to an embodiment of the invention. The physical detector 282 receives data corresponding to region 284. However, a virtual expanded detector 286 having a length 2W in the z axis receives data corresponding to region 288. Thus, within the display volume 290, are FDK VOI 292 corresponding to the physical detector, and Extended FDK VOI 294 corresponding to the virtual expanded detector. FIG. 28B is a line view of the shapes of FDK VOI 292 and Extended FDK VOI 294 separately, for clarity.

Plural images, each of a different portion of a large scanned object, may be successively captured by the inventive system and combined to produce one image of the total object. In particular, data from plural circle scans may be combined with data from one or more line scans, to produce the image of the total object.

FIGS. 29A-F show examples of combining data from plural circle scans with one or more line scans. In each of FIGS. 29A-F, each separate horizontal line 300 corresponds to a single line scan, and each circle 301 corresponds to a single circle scan path (which may include one or more circular scans through that path). Further, the various line and circle scans may be performed in any convenient order.

In addition, the pre-processed circle data may be given different weighting for singly-measured and doubly measured rays in the received circle projection data. For example, when using data from less than a full revolution of redundancy weighting such as described by (Parker, Silver) [17], [18] may be used.

Let $g(\beta, \gamma, \alpha)$ represent a collected line integral along a ray from the source position $\alpha(\beta)$ in direction given by two angles $(\gamma, \alpha)$, where $\gamma$ denotes a fan angle, and $\alpha$ a cone angle. Note that angles $\gamma$ and $\alpha$ are limited by the physical detector, i.e., $-\gamma_m \leq \gamma \leq \gamma_m$ and $-\alpha_m \leq \alpha \leq \alpha_m$. For example, some scanners have $-30° < \gamma < 30°$, $-6° < \alpha < 6°$. Note that for fan beam geometry $g(\beta, \gamma) = g(\beta + \pi + 2\gamma, -\gamma)$. Hence if we acquire the whole revolution of fan beam data (so-called full-scan), each ray is counted twice, and we may weight data with $w(\beta, \gamma) = \frac{1}{2}$. It is not necessary to scan over the whole revolution to reconstruct an image. From relation $g(\beta, \gamma) = g(\beta + \pi + 2\gamma, -\gamma)$, we can see that only $\pi + 2\gamma_m$ reconstruction range is sufficient for exact fan beam reconstruction. Here $\gamma_m$ is the maximum fan angle allowed by detector.

In (Parker) [17] it was suggested to weight data in the minimal complete data set $(\pi + 2\gamma_m)$ such that the discontinuity is as uniformly distributed as possible, and the following weighting function was proposed:

$$w_P(\beta, \gamma) + w_P(\beta + \pi + 2\gamma, -\gamma) = 1 \tag{33}$$

$$w_P(\beta, \gamma) = \begin{cases} \sin^2\left(\frac{\pi}{4}\frac{\beta}{\gamma_m - \gamma}\right), & 0 \leq \beta \leq 2\gamma_m - 2\gamma \\ 1, & 2\gamma_m - 2\gamma \leq \beta \leq \pi - 2\gamma \\ \cos^2\left(\frac{\pi}{4}\frac{\pi + 2\gamma_m - \beta}{\gamma_m + \gamma}\right), & \pi - 2\gamma \leq \beta \leq \pi + 2\gamma_m \end{cases} \tag{34}$$

Here and below, weight is zero if not defined, E.g. $w_P(\beta, \gamma) = 0$ if $\beta < 0$ or $\beta > \pi + 2\gamma_m$. This weighting implies minimal angular reconstruction range $\pi 2\gamma_m$. Note also that by virtually increasing $\gamma_m$ we can obtain larger reconstruction range and hence better noise properties (Silver) [18]. Replacing physical maximum fan angle $\gamma_m$ with virtual $\Gamma$ ($\Gamma \geq \gamma_m$) in equation for $w_P(\beta, \gamma)$, we obtain another weighting function:

$$w_{MHS}(\beta, \gamma) = \begin{cases} \sin^2\left(\frac{\pi}{4}\frac{\beta}{\Gamma - \gamma}\right), & 0 \leq \beta \leq 2\Gamma - 2\gamma \\ 1, & 2\Gamma - 2\gamma \leq \beta \leq \pi - 2\gamma \\ \sin^2\left(\frac{\pi}{4}\frac{\pi + 2\Gamma - \beta}{\Gamma + \gamma}\right), & \pi - 2\gamma \leq \beta \leq \pi + 2\Gamma \end{cases} \tag{35}$$

Note that the Parker weight function is a particular case of MHS weighting, and hence it is preferred to use $w_{MHS}(\beta, \gamma)$ instead of $w_P(\beta, \gamma)$.

Another weighting function was suggested in (Noo)[19], which advantageously allows arbitrary reconstruction range $\Lambda = (\beta_0, \beta_1)$, where $\beta_0$ and $\beta_1$ are starting and ending points of the reconstruction angular range. This weight can be used for ROI reconstruction with reconstruction range less than half-scan. It is given by:

$$w_N(s, \gamma) = \frac{c(\beta)}{\sum_{comp} c(\beta_{comp}, \gamma_{comp})} \tag{36}$$

where, $$\sum_{comp} c(\beta_{comp}, \gamma_{comp}) = c(\beta) + c(\beta + \pi + 2\gamma) + c(\beta - \pi + 2\gamma) + c(\beta + 2\pi) + c(\beta - 2\pi).$$

and the function $c(\beta)$ is given by:

$$c(\beta) = \begin{cases} \cos^2\frac{\pi(\beta - \beta_0 - \Delta\beta)}{2\Delta\beta}, & \beta_0 \leq \beta \leq \beta_0 + \Delta\beta \\ 1, & \beta_0 + \Delta\beta \leq \beta \leq \beta_1 - \Delta\beta \\ \cos^2\frac{\pi(\beta - \beta_1 + \Delta\beta)}{2\Delta\beta}, & \beta_1 - \Delta\beta \leq \beta \leq \beta_1 \end{cases}$$

where $\Delta\beta$ is a smoothing interval that can be chosen as fixed number (20°), or a percentage of the whole reconstruction range ($\beta_0$-$\beta_1$) (but not exceed 50%).

Numerous modifications and variations of the present invention are possible in light of the above teachings. It is therefore to be understood that within the scope of the appended claims, the invention may be practiced otherwise than as specifically described.

The invention claimed is:

1. A volume image reconstruction apparatus, comprising:
a data collection unit configured to receive circle projection data collected by a detector along a circular path with respect to an object, produce pre-processed circle projection data from the received circle projection data, receive line projection data collected by the detector along a linear path with respect to the object, and produce pre-processed line projection data from the received line projection data;
a circle projection data reconstruction unit configured to produce a reconstructed circle path volume image of the object from the pre-processed circle projection data using a reconstruction algorithm that includes a ramp filter;
a line projection data reconstruction unit configured to produce a reconstructed line path volume image of the object from the pre-processed line projection data using a reconstruction algorithm that includes a Hilbert filter; and
an image volume processing unit configured to combine the reconstructed circle path volume image and the reconstructed line path volume image to produce the volume image of the object.

2. The apparatus of claim 1, wherein the linear path is not perpendicular to the plane of the circular path.

3. The apparatus of claim 1, wherein the circle projection data reconstruction unit comprises a backprojecting unit and a directional filtering unit, the backprojecting unit configured to produce the reconstructed circle path volume image based on filtered detector-space data, and the directional filtering unit comprises:
a resampling section configured to resample the pre-processed circle projection data onto filtering curves representing pre-specified filtering directions to produce rebinned data;
a filtering section configured to filter the rebinned data along the filtering curves with the ramp filter to produce filtered data; and
an inverse rebinning section configured to inverse rebin the filtered data to a detector grid to produce the filtered detector-space data.

4. The apparatus of claim 1, wherein the circle projection data reconstruction unit comprises:
a pre-weighting section configured to pre-weight the pre-processed circle projection data by a cosine of a fan angle of the detector and a cosine of a cone angle of the detector to obtain pre-weighted data;
a filtering section configured to filter the pre-weighted data with a Feldkamp, Davis, Kress (FDK) ramp filter along rows of the detector or along pre-specified filtering curves to produce filtered data, and
a backprojecting section configured to backproject the filtered data to produce the reconstructed circle path volume image.

5. The apparatus of claim 1, wherein the circle projection data reconstruction unit comprises:
a pre-weighting section configured to pre-weight the pre-processed data by a cosine of a cone angle of the detector to obtain pre-weighted data;
a hybrid filtering section configured to filter the pre-weighted data with a Zamyatin, Taguchi, Silver (ZTS) ramp filter along rows of the detector or along pre-specified filtering curves to produce filtered data, and
a backprojecting unit configured to backproject the filtered data to produce the reconstructed circle path volume image.

6. The apparatus of claim 1, wherein the data collection unit is further configured to receive circle projection data collected by the detector along the circular path comprising a portion of a full circle, and produce the pre-processed circle data having different weighting for singly-measured and doubly measured rays in the received circle projection data.

7. The apparatus of claim 1, wherein the line projection data reconstruction unit comprises:
a differentiator configured to calculate a derivative of the detected line projection data to produce derivative data;
a rebinning section configured to rebin the derivative data onto filtering curves to produce rebinned data;
a Hilbert filtering section configured to Hilbert filter the rebinned data along the filtering curves to produce filtered data;
an inverse rebinning section configured to inverse rebin the filtered data to a detector grid to produce filtered detector-space data; and
a backprojecting unit configured to backproject the filtered detector-space data to produce the reconstructed line path volume image.

8. The apparatus of claim 1, wherein the line projection data reconstruction unit comprises:
a downsampling section configured to downsample the pre-processed line projection data by a sampling factor selected from 2, 3, 4, or 5 to produce downsampled data;
a differentiator configured to calculate a derivative of the downsampled data to produce derivative data;
a rebinning section configured to rebin the derivative data onto filtering curves to produce rebinned data;
a Hilbert filtering section configured to Hilbert filter the rebinned data along the filtering curves to produce filtered data;
an inverse rebinning section configured to inverse rebin the filtered data to a detector grid to produce filtered detector-space data;
a backprojecting unit configured to backproject the filtered detector-space data to produce a downsampled line path volume image; and
an upsampling unit configured to upsample the downsampled line path volume image by the sampling factor to produce the reconstructed line path volume image.

9. The apparatus of claim 1, further comprising:
an x-ray tube configured to expose the object to a radiation corresponding to an electric current in the x-ray tube, and the electric current is less than or equal to 20 mA; and
a detector configured to produce the line projection data when the object is exposed to the radiation.

10. The apparatus of claim 1, further comprising:
a couch inaccuracy compensating unit configured to adjust a reconstruction parameter based on a correlation between the pre-processed circle projection data and the pre-processed line projection data, and the line projection data reconstruction unit is further configured to produce the reconstructed line path volume image of the object based on the reconstruction parameter.

11. The apparatus of claim 1, wherein the line projection data reconstruction unit comprises:
a differentiator configured to calculate a derivative of the detected line projection data to produce derivative data;
a rebinning section configured to rebin the derivative data onto filtering curves to produce rebinned data;
a Hilbert filtering section configured to Hilbert filter the rebinned data along the filtering curves to produce filtered data; and a backprojecting unit configured to backproject the filtered data directly from the filtering curves to produce the reconstructed line path volume image.

12. The apparatus of claim 1, further comprising:
a source configured to controllably expose the object to a radiation;
a detector configured to produce the line projection data when the object is exposed to the radiation; and
an active collimation unit configured to control the source to expose the object to the radiation with an exposure aperture that corresponds to a part of the detector that receives data to be filtered by a filtering unit.

13. The apparatus of claim 1, wherein the data collection unit is further configured to receive the circle projection data collected by the detector along plural portions of the circular path at different capture times and produce plural pre-processed circle projection data each corresponding to a different capture time, and the image volume processing unit is further configured to produce plural volume images of the object based on the plural pre-processed circle projection data, the apparatus further comprising:
an aggregating unit configured to aggregate the plural volume images of the object from the image volume processing unit and produce aggregated data of the plural volume images; and
a compositing unit configured to produce a composite volume image of the object from the aggregated data of the plural volume images.

14. The apparatus of claim 13, wherein the object exhibits repeated phases, the apparatus further comprising:
an object repetitive mode determining unit configured to identify a phase time when the object exhibits a phase of interest in the repeated phases; and
the compositing unit is further configured to produce the composite volume image based on at least one of the plural volume images corresponding to the phase time when the object exhibits the phase of interest.

15. The apparatus of claim 1, wherein the object exhibits repeated phases, the apparatus further comprising:
an object repetitive mode determining unit configured to identify a phase time when the object exhibits a phase of interest in the repeated phases; and
the data collection unit is further configured to receive the circle projection data collected by the detector along plural portions of the circular path at different capture times and produce plural pre-processed circle projection data each corresponding to a different capture time, and produce the pre-processed circle projection data from the plural pre-processed circle projection data corresponding to the time interval when the object exhibits the phase of interest.

16. The apparatus of claim 1, wherein the data collection unit is further configured to receive the circle projection data collected by the detector along plural circular paths and produce plural pre-processed circle projections each corresponding to a different circle path in the plural circular paths,
the image volume processing unit is further configured to produce plural volume images of portions of the object based on plural reconstructed circle path volume images each corresponding to one of the plural pre-processed circle projections, and combine the plural volume images of the portions of the object to produce the volume image of the object.

17. A method of reconstructing a volume image of an object, the method comprising:
receiving circle projection data collected by a detector along a circular path with respect to the object;
producing pre-processed circle projection data from the received circle projection data;
receiving line projection data collected by the detector along a linear path with respect to the object;
producing pre-processed line projection data from the received line projection data;
producing a reconstructed circle path volume image of the object from the pre-processed circle projection data using a reconstruction algorithm that includes a ramp filter;
producing a reconstructed line path volume image of the object from the pre-processed line projection data using a reconstruction algorithm that includes a Hilbert filter; and
combining the reconstructed circle path volume image and the reconstructed line path volume image to produce the volume image of the object.

18. The method of claim 17, wherein the linear path is not perpendicular to the plane of the circular path.

19. The method of claim 17, wherein the producing the reconstructed circle path volume image further comprises:
resampling the pre-processed circle projection data onto filtering curves representing pre-specified filtering directions to produce rebinned data;
filtering the rebinned data along the filtering curves with the ramp filter to produce filtered data;
inverse rebinning the filtered data to a detector grid to produce the filtered detector-space data; and
backprojecting the filtered detector-space data to produce the reconstructed circle path volume image.

20. The method of claim 17, wherein the producing the reconstructed circle path volume image further comprises:
pre-weighting the pre-processed circle projection data by a cosine of a fan angle of the detector and a cosine of a cone angle of the detector to obtain pre-weighted data;
filtering the pre-weighted data with a Feldkamp, Davis, Kress (FDK) ramp filter along rows of the detector or along pre-specified filtering curves to produce filtered data, and
backprojecting the filtered data to produce the reconstructed circle path volume image.

21. The method of claim 17, wherein the producing the reconstructed circle path volume image further comprises:
pre-weighting the pre-processed data by a cosine of a cone angle of the detector to obtain pre-weighted data;
hybrid filtering the pre-weighted data with a Zamyatin, Taguchi, Silver (ZTS) ramp filter along rows of the detector or along pre-specified filtering curves to produce filtered data, and
backprojecting the filtered data to produce the reconstructed circle path volume image.

22. The method of claim 17, wherein:
the receiving the circle projection data receives the circle projection data collected by the detector along the circular path comprising a portion of a full circle; and
the producing the pre-processed circle projection data produces the pre-processed circle data having different weighting for singly-measured and doubly measured rays in the received circle projection data.

23. The method of claim 17, wherein the producing the reconstructed line path volume image further comprises:
calculating a derivative of the detected line projection data to produce derivative data;
rebinning the derivative data onto filtering curves to produce rebinned data;
Hilbert filtering the rebinned data along the filtering curves to produce filtered data;

inverse rebinning the filtered data to a detector grid to produce filtered detector-space data; and backprojecting the filtered detector-space data to produce the reconstructed line path volume image.

24. The method of claim 17, further comprising:

downsampling the pre-processed line projection data by a sampling factor selected from 2, 3, 4, or 5 to produce downsampled data;

calculating a derivative of the downsampled data to produce derivative data;

rebinning the derivative data onto filtering curves to produce rebinned data;

Hilbert filtering the rebinned data along the filtering curves to produce filtered data;

inverse rebinning the filtered data to a detector grid to produce filtered detector-space data;

backprojecting the filtered detector-space data to produce a downsampled line path volume image; and upsampling the downsampled line path volume image by the sampling factor to produce the reconstructed line path volume image.

25. The method of claim 17, further comprising:

exposing the object to a radiation corresponding to an electric current in an x-ray tube, and the electric current is less than or equal to 20 mA; and producing the line projection data when the object is exposed to the radiation.

26. The method of claim 17, further comprising:

compensating a couch inaccuracy by adjusting a reconstruction parameter based on a correlation between the pre-processed circle projection data and the pre-processed line projection data; and producing the reconstructed line path volume image of the object based on the reconstruction parameter.

27. The method of claim 17, wherein the producing the line path volume image further comprises:

calculating a derivative of the detected line projection data to produce derivative data;

a rebinning section configured to rebin the derivative data onto filtering curves to produce rebinned data;

a Hilbert filtering section configured to Hilbert filter the rebinned data along the filtering curves to produce filtered data; and a backprojecting unit configured to backproject the filtered data directly from the filtering curves to produce the reconstructed line path volume image.

28. The method of claim 17, further comprising:

controllably exposing the object to a radiation;

producing the line projection data when the object is exposed to the radiation; and controlling the exposing to expose the object to the radiation with an exposure aperture that corresponds to a part of the detector that receives data to he filtered by a filtering unit.

29. The method of claim 17, wherein the receiving the circle projection data receives the circle projection data collected by the detector along plural portions of the circular path at different capture times, the producing the pre-processed circle projection data produces plural pre-processed circle projection data each corresponding to a different capture time, and the combining produces plural volume images of the object based on the plural pre-processed circle projection data, the method further comprising:

aggregating the plural volume images of the object;

producing aggregated data of the plural volume images; and producing a composite volume image of the object from the aggregated data of the plural volume images.

30. The method of claim 29, wherein the object exhibits repeated phases, the method further comprising:

identifying a phase time when the object exhibits a phase of interest in the repeated phases; and producing the composite volume image based on at least one of the plural volume images corresponding to the phase time when the object exhibits the phase of interest.

31. The method of claim 17, wherein the object exhibits repeated phases, the method further comprising:

identifying a phase time when the object exhibits a phase of interest in the repeated phases;

receiving the circle projection data collected by the detector along plural portions of the circular path at different capture times;

producing plural pre-processed circle projection data each corresponding to a different capture time; and producing the pre-processed circle projection data from the plural pre-processed circle projection data corresponding to the time interval when the object exhibits the phase of interest.

32. The method of claim 17, wherein:

the receiving the circle projection data receives the circle projection data collected by the detector along plural circular paths;

the producing the pre-processed circle projection data produces plural pre-processed circle projections each corresponding to a different circle path in the plural circular paths;

producing plural volume images of portions of the object based on plural reconstructed circle path volume images each corresponding to one of the plural pre-processed circle projections; and the combining combines the plural volume images of the portions of the object to produce the volume image of the object.

33. A computer-readable medium storing computer program instructions, which when executed by a computer, cause the computer to perform steps comprising:

receiving circle projection data collected by a detector along a circular path with respect to an object;

producing pre-processed circle projection data from the received circle projection data;

receiving line projection data collected by the detector along a linear path with respect to the object;

producing pre-processed line projection data from the received line projection data;

producing a reconstructed circle path volume image of the object from the pre-processed circle projection data using a reconstruction algorithm that includes a ramp filter;

producing a reconstructed line path volume image of the object from the pre-processed line projection data using a reconstruction algorithm that includes a Hilbert filter; and combining the reconstructed circle path volume image and the reconstructed line path volume image to produce a volume image of the object.

* * * * *